United States Patent

Kornberg et al.

[11] Patent Number: 5,874,426
[45] Date of Patent: Feb. 23, 1999

[54] CYCLIC AMINE DERIVATIVES OF SUBSTITUTED QUINOXALINE 2,3-DIONES AS GLUTAMATE RECEPTOR ANTAGONISTS

[75] Inventors: Brian Edward Kornberg; Sham Nikam; Michael Francis Rafferty; Po-Wai Yuen, all of Ann Arbor, Mich.

[73] Assignee: Warner-Lambert Company, Morris Plains, N.J.

[21] Appl. No.: 474,877

[22] Filed: Jun. 7, 1995

[51] Int. Cl.$^6$ .................. C07D 403/06; A61K 31/495
[52] U.S. Cl. ................ 514/212; 514/249; 514/250; 540/599; 544/343
[58] Field of Search ................... 544/343, 354; 540/599; 514/250, 212, 249

[56] References Cited

FOREIGN PATENT DOCUMENTS

| | | |
|---|---|---|
| 572852A1 | 8/1993 | European Pat. Off. . |
| 0627434 | 12/1994 | European Pat. Off. . |
| 6228112-A | 5/1993 | Japan . |
| 93/08188 | 4/1993 | WIPO . |
| 94/26747 | 11/1994 | WIPO . |
| 96/08485 | 3/1996 | WIPO . |

*Primary Examiner*—Mark L. Berch
*Assistant Examiner*—Bruck Kifle
*Attorney, Agent, or Firm*—Elizabeth M. Anderson

[57] ABSTRACT

A novel series of substituted quinoxaline 2,3-diones of Formula I

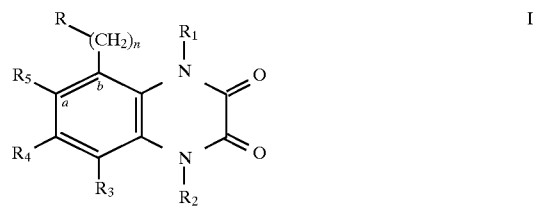

useful as neuroprotective agents are taught. Novel intermediates, processes of preparation, and pharmaceutical compositions containing the compounds are also taught. The compounds are glutamate antagonists and are useful in the treatment of stroke, cerebral ischemia, or cerebral infarction resulting from thromboembolic or hemorrhagic stroke, cerebral vasospasms, hypoglycemia, cardiac arrest, status epilepticus, perinatal asphyxia, anoxia, seizure disorders, pain, Alzheimer's, Parkinson's, and Huntington's Diseases.

9 Claims, 2 Drawing Sheets

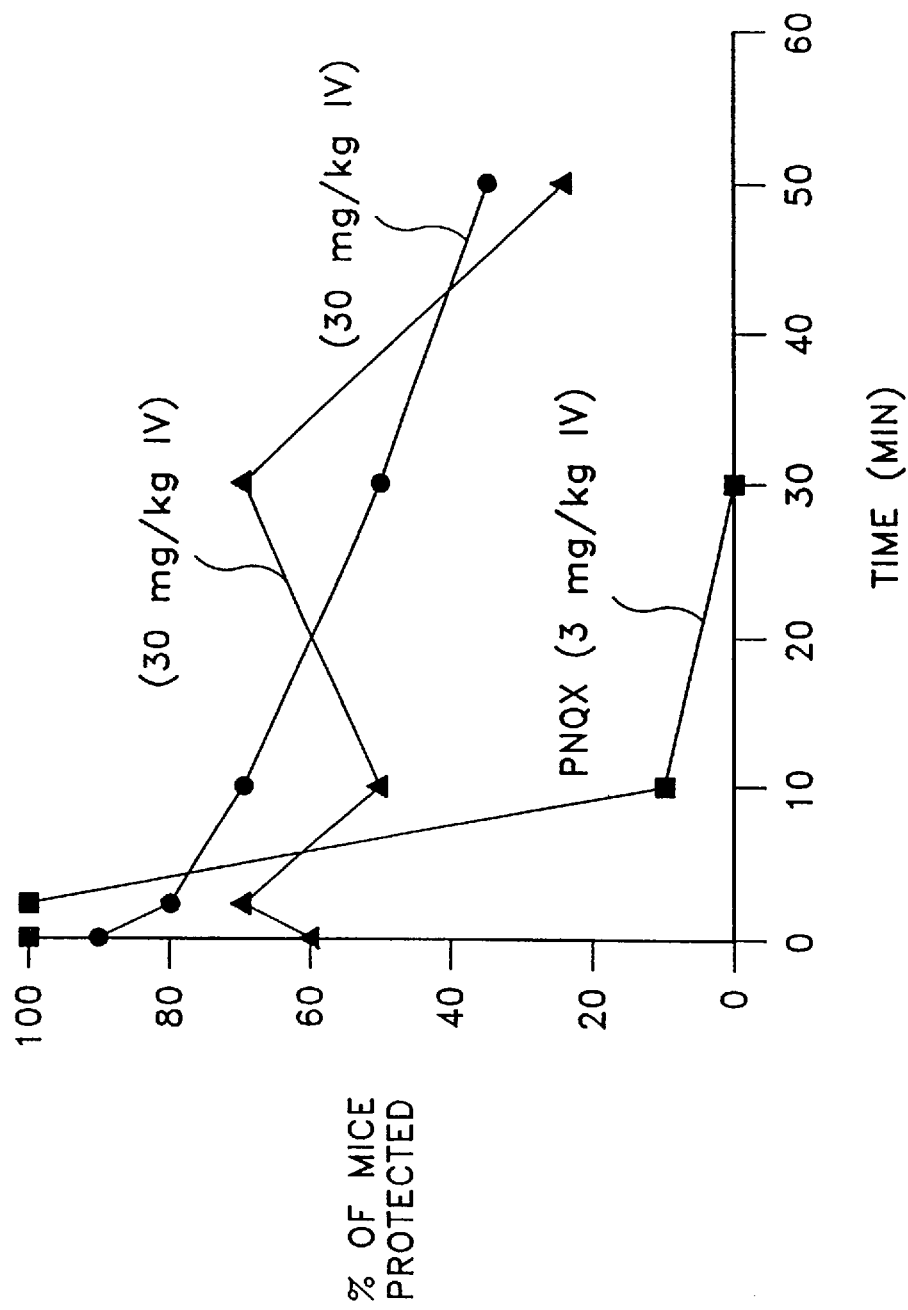

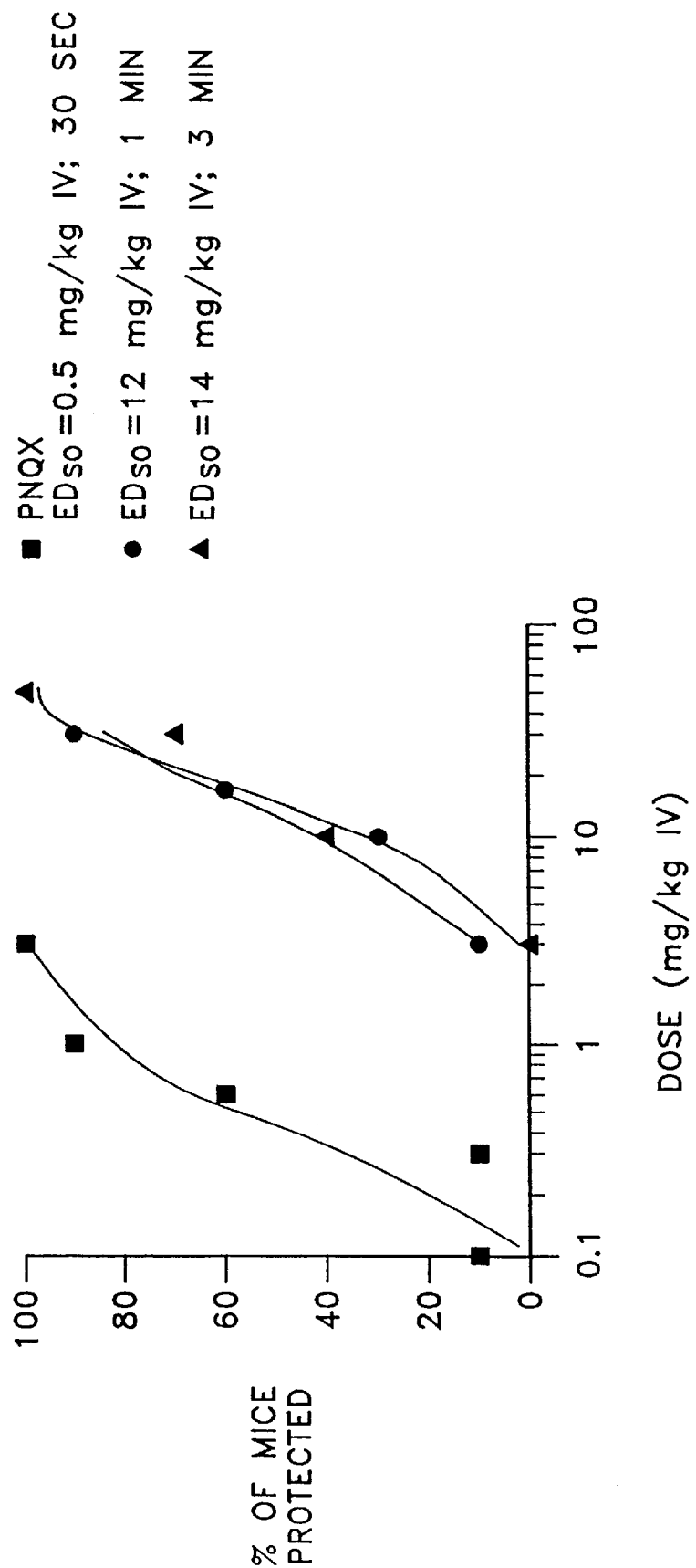
FIG-2 MAXIMAL ELECTROSHOCK DOSE-RESPONSE IN MICE IV

CYCLIC AMINE DERIVATIVES OF SUBSTITUTED QUINOXALINE 2,3-DIONES AS GLUTAMATE RECEPTOR ANTAGONISTS

BACKGROUND OF THE INVENTION

This invention is for novel glutamate receptor antagonists which are new compounds of the 5,6,7,8-substituted quinoxaline 2,3-diones type. The fused ring system is substituted at the a or b position by amino acid derivatives. The compounds are active as excitatory amino acid receptor antagonists acting at glutamate receptors, including either or both N-methyl-D-aspartate (NMDA) receptors and non-NMDA receptors such as the α-amino-3-hydroxy-5-methyl-4-isoxazole propionic acid (AMPA) receptor and the kainate receptor. The invention also relates to the use of those quinoxaline-2,3-diones as neuroprotective agents for treating conditions such as cerebral ischemia or cerebral infarction resulting from a range of phenomena, such as thromboembolic or hemorrhagic stroke, cerebral vasospasms, hypoglycemia, cardiac arrest, status epilepticus, perinatal asphyxia, anoxia such as from drowning, pulmonary surgery, and cerebral trauma, as well as to treat chronic neurodegenerative disorders such as Alzheimer's Disease, Parkinsonism, and Huntington's Disease, and seizure disorders and pain. Therefore, the compounds of the present invention may also be useful in the treatment of schizophrenia, epilepsy, anxiety, pain, and drug addiction. Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA) receptor, the α-amino-3-hydroxy-5-methyl-4-isoxazole propionic acid (AMPA) receptor, and the kainate receptor. AMPA/kainate receptors may be referred to jointly as non-NMDA receptors. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma, as well as lathyrism, Alzheimer's Disease, Parkinson's Disease, and Huntington's Disease.

Several classes of quinoxalinedione derivatives have been disclosed as glutamate (EAA) receptor antagonists. For example, among excitatory amino acid receptor antagonists recognized for usefulness in the treatment of disorders are those that block AMPA receptors (Bigge C. F. and Malone T. C., *Curr. Opin. Ther. Pat.*, 1993:951; Rogawski M. A., *TiPS*, 1993;14:325). AMPA receptor antagonists have prevented neuronal injury in several models of global cerebral ischemia (Li H. and Buchan A. M., *J. Cerebr. Blood Flow Metab.*, 1993;13:933; Nellgard B. and Wieloch T., *J. Cerebr. Blood Flow Metab.*, 1992;12:2) and focal cerebral ischemia (Bullock R., Graham D. I., Swanson S., McCulloch J., *J. Cerebr. Blood Flow Metab.*, 1994;14:466; Xue D., Huang Z.-G., Barnes K., Lesiuk H. J., Smith K. E., Buchan A. M., *J. Cerebr. Blood Flow Metab.*, 1994;14:251). AMPA antagonists have also shown efficacy in models for analgesia (Xu X.-J., Hao J.-X, Seiger A., Wiesenfeld-Hallin Z., *J. Pharmacol. Exp. Ther.*, 1993;267:140), and epilepsy (Namba T., Morimoto K., Sato K., Yamada N., Kuroda S., *Brain Res.*, 1994;638:36; Brown S. E., McCulloch J., *Brain Res.*, 1994;641:10; Yamaguchi S. I., Donevan S. D., Rogawski M. A., *Epilepsy Res.*, 1993;15:179; Smith S. E., Durmuller N., Meldrum B. S., *Eur. J. Pharmacol.*, 1991;201:179). AMPA receptor antagonists have also demonstrated promise in chronic neurodegenerative disorders such as Parkinsonism (Klockgether T., Turski L., Honoŕe T., Zhang Z., Gash D. M., Kurlan R., Greenamyre J. T., *Ann. Neurol.*, 1993;34(4):585–593).

Excitatory amino acid receptor antagonists that block NMDA receptors are also recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain, and anxiety, and may be a significant causal factor in chronic neurodegenerative disorders such as Parkinson's Disease (Klockgether T., Turski L., *Ann. Neurol.*, 1993;34:585–593), human immunodeficiency virus (HIV) related neuronal injury, amyotrophic lateral sclerosis (ALS), Alzheimer's Disease (Francis P. T., Sims N. R., Procter A. W., Bowen D. M., *J. Neurochem.*, 1993;60(5):1589–1604), and Huntington's Disease. (See Lipton S., *TINS*, 1993;16(12):527–532; Lipton S. A., Rosenberg P. A., *New Eng. J. Med.*, 1994;330(9):613–622; and Bigge C. F., *Biochem. Pharmacol.*, 1993;45:1547–1561 and references cited therein.) NMDA receptor antagonists may also be used to prevent tolerance to opiate analgesia or to help control withdrawal symptoms from addictive drugs (Eur. Pat. Appl. 488,959A).

Copending U.S. Ser. No. 08/124,770 refiled as Ser. No. 08/375,059, now abandoned, is a divisional application of Ser. No. 08/443,507 filed May 18, 1995. discloses glutamate receptor antagonist quinoxalinedione derivatives represented by the formula:

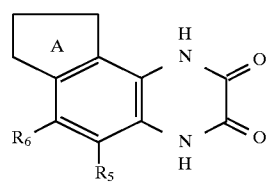

wherein A is a 5 to 7 atom containing ring having a nitrogen which may be substituted by hydrogen, alkyl, or $CH_2CH_2OH$. This application does not disclose or suggest compounds having the instant amino as substituents, or the requisite methodology to prepare the same.

Copending application U.S. Ser. No. 08/404,400 teaches glutamate receptor antagonists which are quinoxalinediones of formula

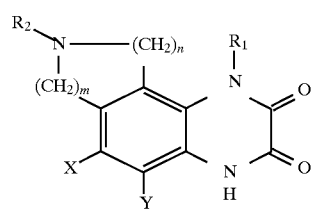

or a pharmaceutically acceptable salt thereof wherein
  $R_1$ is hydrogen, an alkyl, or an alkylaryl;
  X and Y are independently hydrogen, halogen, nitro, cyano, trifluoromethyl, COOH, $CONR_4R_5$, $SO_2CF_3$, $SO_2R_4$ $SONR_4R_5$, alkyl, alkenyl, $(CH_2)_ZCONR_4R_5$, $(CH_2)_ZCOOR_4$, or $NHCOR_4$, wherein $R_4$ and $R_5$ are independently hydrogen, alkyl having 1 to 6 carbon atoms, cycloalkyl, or alkylaryl, and z is an integer from 0 to 4;

$R_2$ is alkylCOOR$_3$, alkylamine, alkylquanidine, aryl, alkylaryl, COalkyl, COalkylaryl, CONR$_3$alkyl, CONR$_3$aryl, CONR$_3$alkylaryl, CSNR$_3$alkyl, CSNR$_3$alkylaryl or a common amino acid moiety joined by an amide bond, wherein $R_3$ is hydrogen, alkyl, or alkylaryl; and m and n are independently 0, 1, or 2 provided that m+n is >1.

This application does not disclose or suggest the compounds of the instant invention having cyclic amines as substituents at the a- or b-positions nor the methodology to prepare them.

JP06228112-A discloses glutamate receptor antagonists which are quinoxaline-2,3(1H,4H)-dione derivatives of formula

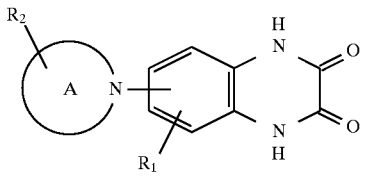

wherein $R_1$ is H, NO$_2$ or CF$_3$;

Ring A is a nitrogen-containing saturated heterocyclic group which may contain sulfur or oxygen;

$R_2$ is H, OH, lower alkoxy, COOH, lower alkoxy carbonyl, NH$_2$, or lower alkoxy carbonyl-amino. This reference does not teach or suggest the instant compounds which must be attached to the quinoxaline dione fused ring system by an alkylene.

WO 93/08188 covers a tricyclic quinoxalinedione of formula

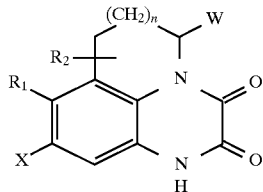

as useful or selective antagonists of glutamate receptors.

European Patent Application 0627434 covers tricyclic quinoxalinedione of Formula I below which are selective antagonists of glycine binding site of the NMDA receptor

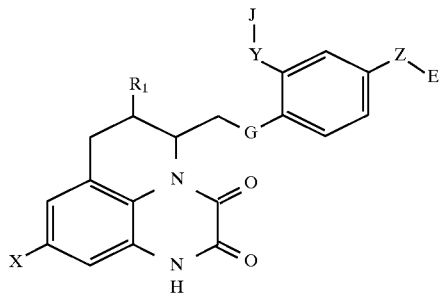

wherein X represents hydrogen, alkyl, halogen, cyano, trifluoromethyl, or nitro;

$R_1$ represents hydrogen, alkyl, cycloalkyl, or cycloalkylalkyl;

G represents —CONR$_2$— or —NR$_2$CO—, wherein $R_2$ represents hydrogen or alkyl;

J represents an acidic group or a group which is convertible thereto in vivo;

E represents a basic group or a group which is convertible thereto in vivo;

Y represents a single bond, alkylene, alkenylene, substituted alkylene, or Y$_1$—Q—Y$_2$, wherein Y$_1$ represents a single bond or alkylene, Y$_2$ represents alkylene, and Q represents a heteroatom selected from oxygen or sulfur; and Z represents alkylene.

WO 94/26747 discloses compounds of Formula I below as useful in the treatment of cerebrovascular disorder

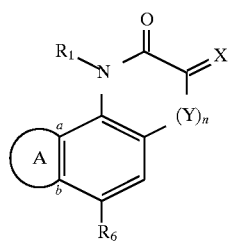

wherein $R_1$ is hydrogen, alkyl or benzyl;

X is O or NOR$_2$, wherein $R_2$ is hydrogen, alkyl, or benzyl;

Y is N—R$_4$, wherein $R_4$ is hydrogen, OH, or alkyl;

n is 0 or 1;

$R_6$ is phenyl, naphthyl, thienyl, pyridyl, all of which may be substituted one or more times with substituents selected from the group consisting of halogen;

CF$_3$, NO$_2$, amino, alkyl, alkoxy, and phenyl; and

A is a ring of 5 to 7 atoms fused with the benzo ring at the positions marked a and b.

The compounds of the instant invention differ from the art in that they provide noncoplanar compounds with greater solubility and, therefore, better ability to penetrate the blood-brain barrier. These are important attributes in pharmaceuticals.

An object of this invention is to provide novel quinoxalinediones with cyclic amines at the a- or b-positions which function as antagonists.

SUMMARY OF THE INVENTION

The present invention is directed to compounds represented by Formula I:

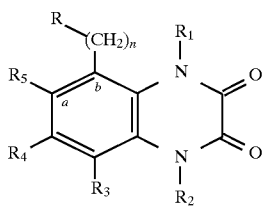

or a pharmaceutically acceptable salt thereof wherein R, $R_1$, $R_2$, $R_3$, $R_4$, $R_5$, and n are as described below.

The instant invention is also related to a pharmaceutical composition containing the compound defined by Formula I in an amount effective to treat cerebrovascular disorders responsive to the blockade of glutamate receptors (such as the α-amino-3-hydroxy-5-methyl-4-isoxazole propionic acid (AMPA) receptor and the kainate receptor), and a pharmaceutically acceptable carrier. Exemplary disorders responsive to such treatment include cerebral ischemia caused by cerebral trauma, stroke, hypoglycemia, heart attack, and surgery; anxiety and schizophrenia; and chronic neurodegenerative disorders such as Huntington's Disease, ALS, Parkinsonism, and Alzheimer's Disease. The pharmaceutical composition of this invention may also be employed as an analgesic or the treatment of epilepsy.

The invention further relates to a method of treating cerebrovascular disorders responsive to antagonism of glutamate receptors NMDA by administering a compound of above-defined Formula I in a unit dosage form.

Another object of this invention is to provide a method of treating disorders responsive to the antagonism of glutamate or aspartate receptors in a human by administering a pharmaceutically effective amount of the 2,3-quinoxalinediones of this invention.

Another object of this invention is to provide novel methods of preparing the 2,3-quinoxalinediones.

A further object of this invention is directed to novel intermediates useful in the preparation of the 2,3-quinoxalinediones of this invention.

BRIEF DESCRIPTION OF THE DRAWINGS

FIG. 1. Maximal Electroshock Time Course with Compound 1, Compound 2, and PNQX is 1,4,7,8,9,10-hexahydro-7-methyl-6-nitro-pyrido[3,4-f]quinoxaline-2,3-dione in Mice IV FIG. 2. Maximal Electroshock Dose-Response with PNQX, Compounds 4 and 1 in Mice IV

DETAILED DESCRIPTION OF THE INVENTION

The substituted quinoxaline-2,3-diones of the instant invention are those of Formula I or a pharmaceutically acceptable salt thereof wherein
R is a cyclic amine;
n is an integer of from 1 to 4;
$R_1$ is hydrogen,
  alkyl,
  aralkyl,
  carboxyalkyl,
  phosphonoalkyl, or
  phosphonoalkyl;
$R_2$ is hydrogen, hydroxy, or amino;
$R_3$ and $R_4$ are each independently
  hydrogen,
  alkyl,
  cycloalkyl,
  alkenyl,
  halogen,
  haloalkyl,
  nitro,
  cyano,
  $SO_2CF_3$,
  $CH_2SO_2R_6$,
  $(CH_2)_mCO_2R_6$,
  $(CH_2)_mCONR_7R_8$,
  $(CH_2)_mSO_2NR_7R_8$, or
  $NHCOR_6$ wherein m is an integer of from 0 to 4, and $R_6$, $R_7$, and $R_8$ are each independently selected from hydrogen, alkyl, cycloalkyl, haloalkyl, or aralkyl;
$R_5$ is hydrogen,
  alkyl,
  alkenyl,
  cycloalkyl,
  halogen,
  haloalkyl,
  aryl,
  aralkyl,
  heteroaryl,
  nitro,
  cyano,
  $SO_2CF_3$,
  $(CH_2)_mCO_2R_9$,
  $(CH_2)_mCONR_9R_{10}$,
  $SONR_9R_{10}$, or
  $NHCOR_9$;
m is an integer of from 0 to 4;
$R_9$ and $R_{10}$ are each independently hydrogen, alkyl, cycloalkyl, haloalkyl, or aralkyl; and
$R_5$ may be at the a-position and $R—(CH_2)_n$— at the b-position on the ring.

Preferred compounds are those of Formula I wherein R is a mono- or bi-cyclic ring unsubstituted or substituted by from 1 to 4 substituents, R is attached to the quinoxaline ring through $N(—CH_2)_n$ and at the a- or b-position and R is of from 4 to 7 atoms or of from 8 to 12 atoms
  wherein $R_{11}$ is from 1 to 4 substituents independently selected from
    hydrogen,
    hydroxy,
    hydroxyalkyl,
    alkyl,
    alkoxy,
    alkoxyalkyl,
    $—NR_{13}R_{14}$,
    aminoalkyl,
    alkenyl,
    alkynyl,
    thiol,
    thioalkyl,
    alkylthioalkyl,
    aryl,
    aralkyl, heteroaryl,
heteroaralkyl,
cycloalkyl,
—SO$_2$R$_{15}$,
—SO$_2$NR$_{13}$R$_{14}$,
—(CH$_2$)$_n$SO$_2$NR$_{13}$R$_{14}$, and
—(CH$_2$)$_n$SO$_2$R$_{15}$;
wherein R$_{13}$ and R$_{14}$ are independently selected from
hydrogen,
alkyl,
cycloalkyl,
heterocycloalkyl,
aralkyl, and
aryl;
R$_{15}$ is hydroxy, alkoxy, —NR$_{13}$R$_{14}$, or haloalkyl;
R$_{11}$ may be 2 substituents attached at the same carbon;
X and Y are each independently
carbon which is substituted by hydrogen, halogen, haloalkyl, alkyl, alkoxy, alkoxyalkyl, NR$_{13}$R$_{14}$, aminoalkyl, aralkyl, aryl, heteroaryl, heteroaralkyl, cycloalkyl, heterocycloalkyl, hydroxy, and hydroxyalkyl,
—O—,
—S—,
—SO$_2$—,
—NR$_{16}$—,
wherein R$_{16}$ is alkyl, hydrogen, aralkyl, heteroaralkyl, aryl, heteroaryl, cycloalkyl, heterocycloalkyl, —C(O)OR$_{17}$, —C(O)R$_{17}$, —SO$_2$R$_{18}$, —SO$_2$NR$_{19}$R$_{20}$, —CH$_2$SO$_2$R$_{18}$, —CH$_2$SO$_2$NR$_{19}$R$_{20}$,
wherein R$_{17}$ is alkyl, aralkyl, cycloalkyl, heterocycloalkyl, aryl, or heteroaryl;
R$_{18}$ is alkyl, aralkyl, hydroxyl, or alkoxy;
R$_{19}$ and R$_{20}$ are each independently hydrogen and alkyl.

Bicyclic structures encompassed in this invention include spiro ring structures, wherein both ends of a second ring are attached to the same carbon unit on the parent ring.

For monocyclic and bicyclic structures wherein X or Y represent a carbon atom, the structure may also include an integral double bond.

More preferred are those of Formula I wherein
R is

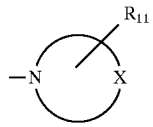

of from 4 to 7 atoms where
X is
carbon substituted by hydrogen, haloalkyl, alkyl, alkoxy, alkoxyalkyl, NR$_{13}$R$_{14}$, aminoalkyl, cycloalkyl, heterocycloalkyl, hydroxy, and hydroxyalkyl,
—O—,
—NR$_{16}$—, and
—C(O)—;
R$_{11}$ is absent,
hydrogen,
alkyl,
alkoxy,
alkoxyalkyl,
NR$_{13}$R$_{14}$,
aminoalkyl,
aralkyl,
aryl,
heteroaryl,
heteroaralkyl,
cycloalkyl,
heterocycloalkyl,
hydroxy, or
hydroxyalkyl,
R$_{11}$ may also represent two independent alkyl substituents to form a gem-dialkyl arrangement,
where X represents carbon, an integral double bond may be located between the C$_3$ and C$_4$ carbons of 5- to 7-membered rings.
Still more preferred are those of Formula I
wherein R is

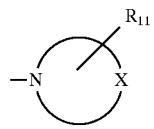

of from 4 to 7 atoms where
X is
carbon substituted by hydrogen, alkyl, NR$_{13}$R$_{14}$, aminoalkyl, cycloalkyl, and heterocycloalkyl,
—O—,
—NR$_{16}$—, and
—C(O) —;
R$_{11}$ is absent,
hydrogen,
hydroxy,
hydroxyalkyl,
alkyl,
alkoxy,
alkoxyalkyl,
—NR$_{13}$R$_{14}$,
aminoalkyl,
cycloalkyl, or
heterocycloalkyl;
R$_{11}$ may also represent two independent alkyl substituents to form a gem-dialkyl arrangement,
where X represents carbon, an integral double bond may be located between the C$_3$ and C$_4$ carbons of 5- to 7-membered rings.
R$_1$ is hydrogen;
R$_2$ is hydrogen or hydroxy;
R$_3$ and R$_4$ are each independently
hydrogen,
alkyl, or
nitro;
R$_5$ is hydrogen,
alkyl,
cycloalkyl,
halo, or
nitro.
Most preferred are selected from
6-Methyl-5-pyrrolidin-1-ylmethyl-7-nitro-1,4-dihydroquinoxaline-2,3-dione,
6-Methyl-5-(2-methyl-pyrrolidin-1-ylmethyl)-7-nitro-1,4-dihydroquinoxaline-2,3-dione,
5-(2,5-Dimethyl-pyrrolidin-1-ylmethyl)-6-methyl-7-nitro-1,4-dihydroquinoxaline-2,3-dione,
6-Methyl-7-nitro-5-piperidin-1-ylmethyl-1,4-dihydroquinoxaline-2,3-dione, 6-Methyl-5-(2-methyl-piperidin-1-ylmethyl)-7-nitro-1,4-dihydroquinoxaline-2,3-dione, 6-Methyl-5-(4-methyl-piperidin-1-ylmethyl)-7-nitro-1,4-dihydroquinoxaline-2,3-dione, 5-(3,5-Dimethyl-piperidin-1-ylmethyl)-6-methyl-7-nitro-1,4-dihydroquinoxaline-2,3-dione, 5-(3-Azaspiro [5.5]undec-3-ylmethyl)-6-methyl-7-nitro-1,4-dihydroquinoxaline-2,3-dione, 5-(1,4-Dioxa-8-azaspiro [4,5]dec-8-ylmethyl)-6-methyl-7-nitro-1,4-dihydroquinoxaline-2,3-dione, 6-Methyl-5-morpholin-4-ylmethyl-7-nitro-1,4-dihydroquinoxaline-2,3-dione, 6-Methyl-5-(4-methyl-piperazin-1-ylmethyl)-7-nitro-1,4-dihydroquinoxaline-2,3-dione, 5-Azepan-1-ylmethyl-6-methyl-7-nitro-1,4-dihydroqinoxaline-2,3-dione, 6-Methyl-7-nitro-5-(octahydroquinolin-1-ylmethyl)-1,4-dihydroquinoxaline-2,3-dione, and 6-Methyl-7-nitro-5-(octahydroisoquinolin-2-ylmethyl)-1,4-dihydroquinoxaline-2,3-dione.

Other preferred compounds of the invention are those of Formula I wherein R

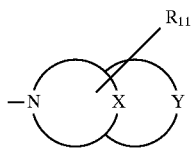

of from 8 to 12 atoms;

X and Y are each independently as described above;

$R_{11}$ is absent,
hydrogen,
alkyl,
alkoxy,
alkoxyalkyl,
$NR_{13}R_{14}$,
aminoalkyl,
aralkyl,
aryl,
heteroaryl,
heteroaralkyl,
cycloalkyl,
heterocycloalkyl,
hydroxy, and
hydroxyalkyl;

$R_1$ is hydrogen;

$R_2$ is hydrogen or hydroxy;

$R_3$ and $R_4$ are each independently
hydrogen,
alkyl, and
nitro;

$R_5$ is hydrogen,
alkyl,
cycloalkyl,
halogen, and
nitro.

The compounds of Formula I are capable of further forming pharmaceutically acceptable acid addition salts. These forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, isethionate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention may exist as a mixture of cis and trans isomers or as the individual cis and trans isomers or R and S stereoisomers. The mixture of isomers as well as the individual isomers are intended to be encompassed within the scope of the present invention.

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "carboxyalkyl" means alkyl as above and attached to a carboxy group.

The term "phosphoroalkyl" means alkyl as above and attached to a phosphoro group.

The term "phosphonoalkyl" means alkyl as above and attached to a phosphono group.

The term "alkenyl" means a straight or branched unsaturated hydrocarbon radical having from 3 to 6 carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl, and the like.

Alkynyl means a straight or branched unsaturated hydrocarbon radical of from 2 to 6 carbon atoms and includes but is not limited to ethynyl, 2,3-propynyl, 1,2-propynyl, and 3,4-butynyl.

"Alkoxy" is O-alkyl of from 1 to 6 carbon atoms as defined above for "alkyl".

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, or 1,3-benzodioxol-5-yl.

The term "aralkyl" means aryl and alkyl as defined above and includes but is not limited to benzyl, 2-phenylethyl, and 3-phenylpropyl; a preferred group is phenyl.

The term "heteroaryl" means a heteroaromatic radical which is 2-, 3-, or 4-pyridinyl, 2-, 4-, or 5-pyrimidinyl, 2- or 3-thienyl, isoquinolines, quinolines, pyrroles, indoles, and thiazoles.

"Halogen" is fluorine, chlorine, bromine, or iodine.

The term "haloalkyl" means halogen and alkyl as defined above, for example, but not limited to, trifluoromethyl and trichloromethyl.

"Alkylaryl" means aryl as defined above and alkyl as defined above, for example, but not limited to benzyl, 2-phenylethyl, 3-phenylpropyl; a preferred group is benzyl.

The term "heterocycloalkyl" means a nonaromatic ring with from 4 to 7 members, with up to 4 heteroatoms for example, N, O, and S.

Spiro rings include but are not limited to 5- to 7-membered carbocyclic or heterocyclic ring with up to 4 heteroatoms.

R in Formula I may be defined as follows. These groups are merely illustrative of the invention.

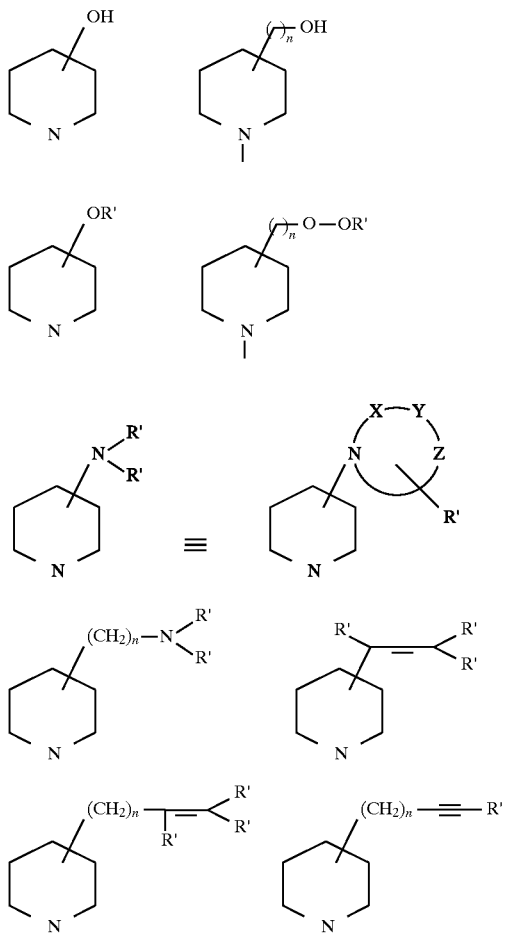
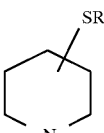
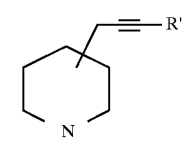
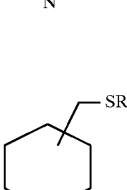
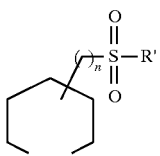
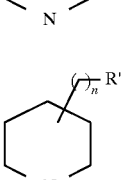
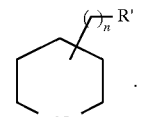

The compounds of the invention exhibit valuable biological properties because of their strong excitatory amino acid (EAA) antagonizing properties at one of several binding sites on glutamate receptors: the AMPA ((RS)-amino-3-hydroxy-5-methyl-4-isoxazole propionic acid (or kainic acid) binding site on AMPA (non-NMDA) receptors or the glycine site of NMDA receptors.

The compounds of the present invention exhibit binding affinity for the AMPA receptors measured as described in Honoŕ T., et al., *Neuroscience Letters*, 1985;54:27–32. Preferred compounds demonstrate $IC_{50}$ values <100 μM in this assay. The compounds of the present invention exhibit binding affinity for the kainate site (non-NMDA receptor) measured as described in London E. D. and Coyle J., *Mol. Pharmacol.*, 1979;15:492. The compounds of the present invention exhibit binding affinity for the glycine site of the NMDA receptor measured as described in Jones S. M., et al., *Pharmacol. Methods*, 1989;21:161. To measure functional AMPA antagonist activity, the effects of the agent on AMPA-induced neuronal damage in primary cortical neuronal cultures was examined using techniques similar to those outlined by Koh J.-Y., et al., *J. Neurosci*, 1990;10:693. In addition, the neuronal damage produced by long-term exposure to 100 μM AMPA may be measured by the release of the cytosolic enzyme lactate dehydrogenase (LDH).

Selected compounds of the present invention were tested by one or more of the above-described assays. The data obtained in the assays is set forth in Tables 1–4 below. The $IC_{50}$ values set forth in Tables 1–4 are a measure of the concentration (μM) of the test substance which inhibits 50% of an induced release from the tested receptors.

TABLE 1

Quinoxalinediones With Cyclic Amine

| Compound | Structure | IC₅₀ μM | |
|---|---|---|---|
| | | AMPA | KA |
| 6-Methyl-5-pyrrolidin-1-ylmethyl-7-nitro-1,4-dihydroquinoxaline-2,3-dione | pyrrolidine | 0.22 | 4.52 |
| 6-Methyl-5-(2-methylpyrrolidin-1-ylmethyl)-7-nitro-1,4-dihydroquinoxaline-2,3-dione | 2-methylpyrrolidine | 0.37 | 6.11 |
| 5-(2,5-Dimethylpyrrolidin-1-ylmethyl)-6-methyl-7-nitro-1,4-dihydroquinoxaline-2,3-dione | 2,5-dimethylpyrrolidine | 0.74 | 2.84 |
| 6-Methyl-5-(piperidin-1-ylmethyl)-7-nitro-1,4-dihydroquinoxaline-2,3-dione | piperidine | 0.29 | 4.11 |
| 6-Methyl-5-(2-methyl piperidin-1-ylmethyl)-7-nitro-1,4-dihydro quinoxaline-2,3-dione | 2-methylpiperidine | 0.49 | 8.28 |
| 6-Methyl-5-(4-methyl piperidin-1-ylmethyl)-7-nitro-1,4-dihydro quinoxaline-2,3-dione | 4-methylpiperidine | 0.42 | 9.95 |
| 5-(3,5-Dimethylpiperidin-1-ylmethyl)-6-methyl-7-nitro-1,4-dihydroquinoxaline-2,3-dione | 3,5-dimethylpiperidine | | |
| 5-(3-Azaspiro[5,5]undec-3-ylmethyl)-6-methyl-7-nitro-1,4-dihydroquinoxaline-2,3-dione | 3-azaspiro[5,5]undecane | 0.486 | 6.54 |
| 5-(1,4-Dioxa-8-azaspiro[4,5]dec-8-ylmethyl)-6-methyl-7-nitro-1,4-dihydroquinoxaline-2,3-dione | 1,4-dioxa-8-azaspiro[4,5]decane | | |
| 6-Methyl-5-(morpholin-1-ylmethyl)-7-nitro-1,4-dihydroquinoxaline-2,3-dione | morpholine | 0.572 | 9.083 |

TABLE 1-continued

Quinoxalinediones With Cyclic Amine

| Compound | Structure | IC₅₀ μM | |
|---|---|---|---|
| | | AMPA | KA |
| 6-Methyl-5-(4-methyl piperazin-1-ylmethyl)-7-nitro-1,4-dihydro quinoxaline-2,3-dione | —N(piperazine)N—CH₃ | 2.47 | 13.2 |
| 5-(Azepan-1-ylmethyl)-6-methyl-7-nitro-1,4-dihydroquinoxaline-2,3-dione | —N(azepane) | 0.899 | 3.695 |
| 6-Methyl-7-nitro-5-(octahydroquinolin-1-ylmethyl)-1,4-dihydro quinoxaline-2,3-dione | —N(octahydroquinoline) | | |
| 6-Methyl-7-nitro-5-(octahydroisoquinolin-2-ylmethyl)-1,4-dihydro quinoxaline-2,3-dione | —N(octahydroisoquinoline) | | |

TABLE 2 o-Nitroaniline Derivatives

| Compound | Structure | Yield % | MS (CI) M + 1 |
|---|---|---|---|
| 3-Methyl-6-nitro-2-pyrrolidin-1-ylmethyl-phenylamine | 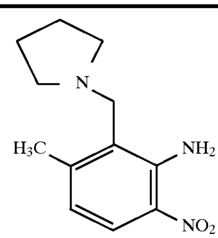 | 80 | 236 |
| 3-Methyl-2-(2-methylpyrrolidin-1-ylmethyl)-6-nitro-phenylamine | 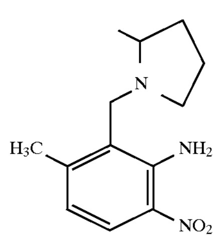 | 62 | 250 |

TABLE 2-continued o-Nitroaniline Derivatives

| Compound | Structure | Yield % | IC$_{50}$ μM MS (CI) M + 1 |
|---|---|---|---|
| 2-(2,5-Dimethyl-pyrrolidin-1-ylmethyl)-3-methyl-6-nitro-phenylamine | 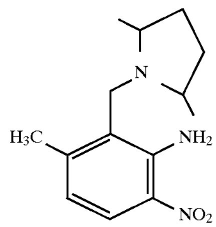 | 65 | 264 |
| 3-Methyl-6-nitro-2-piperidin-1-ylmethyl-phenylamine | 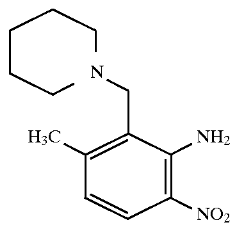 | 84 | 250 |
| 3-Methyl-2-(2-methyl-piperidin-1-ylmethyl)-6-nitro-phenylamine | 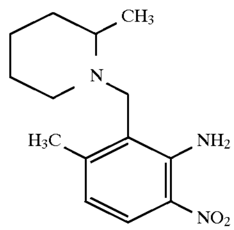 | 49 | 264 |
| 3-Methyl-2-(4-methyl-piperidin-1-ylmethyl)-6-nitro-phenylamine | 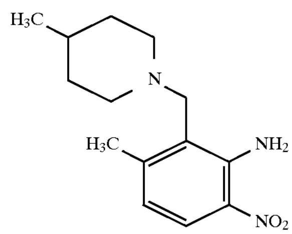 | 74 | 264 |
| 2-(3,5-Dimethyl-piperidin-1-ylmethyl)-3-methyl-6-nitro-phenylamine | 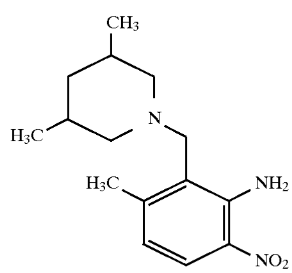 | 76 | 278 |
| 2-(3-Azaspiro[5.5]undec-3-ylmethyl)-3-methyl-6-nitro-phenylamine | 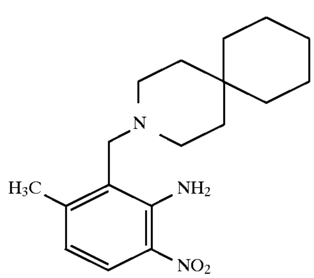 | 93 | 318 |

TABLE 2-continued o-Nitroaniline Derivatives

| Compound | Structure | Yield % | MS (CI) M + 1 |
|---|---|---|---|
| 2-(1,4-Dioxa-8-azaspiro[4,5]dec-8-ylmethyl)-3-methyl-6-nitro-phenylamine | 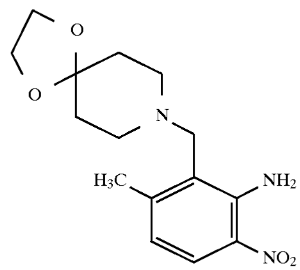 | 71 | 308 |
| 3-Methyl-2-morpholin-4-ylmethyl-6-nitro-phenyl amine | 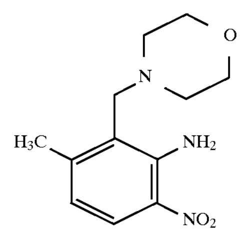 | 43* | 252 |
| 3-Methyl-2-(4-methyl-piperazin-1-ylmethyl)-6-nitro-phenylamine | 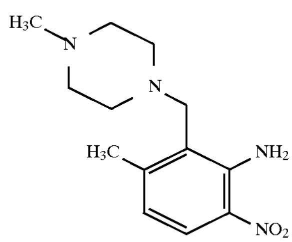 | 77 | 265 |
| 2-Azepan-1-ylmethyl-3-methyl-6-nitro-phenylamine | 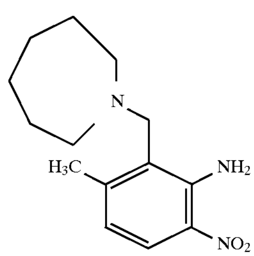 | 79 | 264 |
| 3-Methyl-6-nitro-2-(octahydroquinolin-1-ylmethyl)-phenylamine | 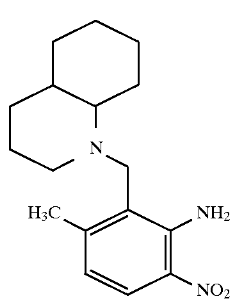 | 51 | 304 |

TABLE 2-continued o-Nitroaniline Derivatives

| Compound | Structure | Yield % | IC$_{50}$ µM MS (CI) M + 1 |
|---|---|---|---|
| 3-Methyl-6-nitro-2-(octahydroisoquinolin-2-ylmethyl)-phenylamine | | 80 | 304 |

*Prepared via Scheme 2 (PBr$_3$)

TABLE 3

Quinoxaline-2,3-diones

| Compound | | Yield % | IC$_{50}$ µM MS (CI) M + 1 |
|---|---|---|---|
| 6-Methyl-5-pyrrolidin-1-ylmethyl-1,4-dihydro-quinoxaline-2,3-dione | | 69 | 260 |
| 5-(2-Methyl-pyrrolidin-1-ylmethyl)-1,4-dihydro-quinoxaline-2,3-dione | | 76 | 274 |
| 5-(2,5-Dimethyl-pyrrolidin-1-ylmethyl)-6-methyl-1,4-dihydro-quinoxaline-2,3-dione | | 52 | 288 |

TABLE 3-continued

Quinoxaline-2,3-diones

| Compound | | Yield % | MS (CI) M + 1 |
|---|---|---|---|
| 6-Methyl-5-piperidin-1-ylmethyl-1,4-dihydro-quinoxaline-2,3-dione | | 64 | 274 |
| 6-Methyl-5-(2-methyl-piperidin-1-ylmethyl)-1,4-dihydro-quinoxaline-2,3-dione | | 63 | 288 |
| 6-Methyl-5-(4-methyl-piperidin-1-ylmethyl)-1,4-dihydro-quinoxaline-2,3-dione | | 66 | 289 |
| 5-(3,5-Dimethyl-piperidin-1-ylmethyl)-6-methyl-1,4-dihydro-quinoxaline-2,3-dione | | 59 | 302 |
| 5-(3-Aza-spiro[5.5]undec-3-ylmethyl)-6-methyl-1,4-dihydro-quinoxaline-2,3-dione | | 69 | 342 |

IC$_{50}$ μM

TABLE 3-continued

Quinoxaline-2,3-diones

| Compound | | Yield % | IC$_{50}$ μM MS (CI) M + 1 |
|---|---|---|---|
| 5-(1,4-Dioxa-8-aza-spiro[4,5]dec-8-ylmethyl)-6-methyl-1,4-dihydro-quinoxaline-2,3-dione | | 51 | 332 |
| 6-methyl-5-morpholin-4-ylmethyl-7-nitro-1,4-dihydro-quinoxaline-2,3-dione | | 67 | 276 |
| 6-Methyl-5-(4-methyl-piperazin-1-ylmethyl)-1,4-dihydro-quinoxaline-2,3-dione | | 41 | 289 |
| 5-Azepan-1-ylmethyl-6-methyl-1,4-dihydro-quinoxaline-2,3-dione | | 39 | 288 |
| 6-Methyl-5-(octahydro-quinolin-1-ylmethyl)-1,4-dihydro-quinoxaline-2,3-dione | | 79 | 328 |

TABLE 3-continued

Quinoxaline-2,3-diones

| Compound | | Yield % | MS (CI) M + 1 | IC$_{50}$ μM |
|---|---|---|---|---|
| 6-Methyl-5-(octahydro-isoquinolin-2-ylmethyl)-1,4-dihydro-quinoxaline-2,3-dione | | 76 | 328 | |

TABLE 4

7-Nitro-quinoxaline-2,3-diones

| Compound | | Yield % | MS (CI) M + 1 | IC$_{50}$ μM |
|---|---|---|---|---|
| 6-Methyl-5-pyrrolidin-1 ylmethyl-7-nitro-1,4-dihydroquinoxaline-2,3-dione | | 92 | 305 | |
| 6-Methyl-5-(2-methyl-pyrrolidin-1-ylmethyl)-7-nitro-1,4-dihydro quinoxaline-2,3-dione | | 47 | 319 | |
| 5-(2,5-Dimethyl-pyrrolidin-1-ylmethyl)-6-methyl-7-nitro-1,4-dihydroquinoxaline-2,3-dione | | 41 | 331 | |

TABLE 4-continued

7-Nitro-quinoxaline-2,3-diones

| Compound | | Yield % | IC$_{50}$ μM MS (CI) M + 1 |
|---|---|---|---|
| 6-Methyl-7-nitro-5-piperidin-1-ylmethyl-1,4-dihydro-quinoxaline-2,3-dione | | 84 | 319 |
| 6-Methyl-5-(2-methyl-piperidin-1-ylmethyl)-7-nitro-1,4-dihydroquinoxaline-2,3-dione | | 77 | 333 |
| 6-Methyl-5-(4-methyl-piperidin-1-ylmethyl)-7-nitro-1,4-dihydroquinoxaline-2,3-dione | | 68 | 333 |
| 5-(3,5-Dimethyl-piperidin-1-ylmethyl)-6-methyl-7-nitro-1,4-dihydroquinoxaline-2,3-dione | | 79 | 347 |
| 5-(3-Azaspiro[5.5]undec-3-ylmethyl)-6-methyl-7-nitro-1,4-dihydroquinoxaline-2,3-dione | | 91 | 387 |

TABLE 4-continued

7-Nitro-quinoxaline-2,3-diones

| Compound | | Yield % | IC$_{50}$ μM MS (CI) M + 1 |
|---|---|---|---|
| 5-(1,4-Dioxa-8-azaspiro[4,5]dec-8-ylmethyl)-6-methyl-7-nitro-1,4-dihydroquinoxaline-2,3-dione | | 29 | 377 |
| 6-Methyl-5-morpholin-4-ylmethyl-7-nitro-1,4-dihydroquinoxaline-2,3-dione | | 56 | 321 |
| 6-Methyl-5-(4-methyl-piperazin-1-ylmethyl)-7-nitro-1,4-dihydroquinoxaline-2,3-dione | | 64 | 334 |
| 5-Azepan-1-ylmethyl-6-methyl-7-nitro-1,4-dihydroqinoxaline-2,3-dione | | 59 | 333 |
| 6-Methyl-7-nitro-5-(octahydroquinolin-1-ylmethyl)-1,4-dihydroquinoxaline-2,3-dione | | 59 | 373 |

TABLE 4-continued

7-Nitro-quinoxaline-2,3-diones

| Compound | | Yield % | IC$_{50}$ µM MS (CI) M + 1 |
|---|---|---|---|
| 6-Methyl-7-nitro-5-(octahydroisoquinolin-2-ylmethyl)-1,4-dihydro quinoxaline-2,3-dione | | 88 | 373 |

Additionally, as a preliminary indicator of in vivo CNS activity related to anticonvulsant activity and potential neuroprotection, a maximal electroshock assay in CF-1 strain mice (20–25 g) was performed with corneal electrodes by conventional methods as described previously (Krall, et al., *Epilepsia*, 1988;19:409–428). The compounds of this invention generally demonstrated ED$_{50}$ values of <50 mg/kg.

DETAILED DESCRIPTION OF THE DRAWINGS

FIG. 1 shows the maximal electroshock time course with Compounds 1 and 4 of the instant invention and the standard PNQX in ten mice given in a dose of 30 mg/kg IV. The graph is the t of mice protected versus the time in minutes. The ■ is PNQX at 3 mg/kg IV, the ▲ is Compound 1, and the ● is Compound 4.

FIG. 2 shows the maximal electroshock dose-response with PNQX and Compounds 1 and 4 of the instant invention in ten mice. The ■ is PNQX with an ED$_{50}$ of 0.5 mg/kg IV; 30 seconds, ● is Compound 4 with an ED$_{50}$ of 12 mg/kg IV; 60 seconds, and ▲ is Compound 1 with an ED$_{50}$ of 14 mg/kg IV; 180 seconds.

In particular see FIGS. 1 and 2 wherein, when compared with the standard, a tricyclic quinoxalinedione AMPA antagonist (PNQX), Compounds 1 and 4 of the instant invention show surprising results.

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprises conventional ingredients in conventional proportions, with or without additional active compounds or principles, and such unit dosage forms may contain any suitable effective amount of the active ingredient commensurate with the intended daily dosage range to be employed. Tablets containing 10 mg of active ingredients or, more broadly, 0.1 to 100 mg per tablet, and accordingly suitable representative unit dosage forms.

Solid forms of pharmaceutical compositions for PO administration and injectable solutions are preferred.

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino-acid-dependent psychosis, excitatory amino-acid- dependent anoxia, excitatory amino-acid-dependent ischemia, excitatory amino-acid-dependent Parkinsonism, excitatory amino-acid-dependent convulsions, and excitatory amino-acid-dependent migraine. Suitable dosage ranges are 0.1 to 1000 mg daily, 10 to 50 mg daily, and especially 30 to 100 mg daily, dependent as usual upon the exact mode of administration, form in which administered, the indication toward which the administration is directed, the subject involved, and the body weight of the subject involved, and further, the preference and experience of the physician or veterinarian in charge.

The schemes and examples which follow are intended as an illustration of certain preferred embodiments of the invention, and no limitation of the invention is implied.

General Scheme I

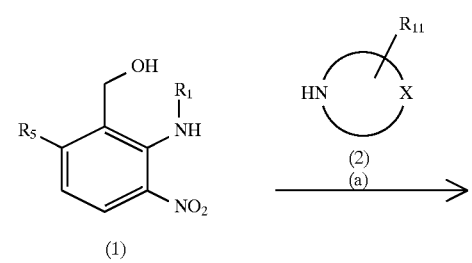

Utaka M., et al. Bull. Chem Soc., Japan, 1977; 50:3276–3280.

General Scheme I (continued)

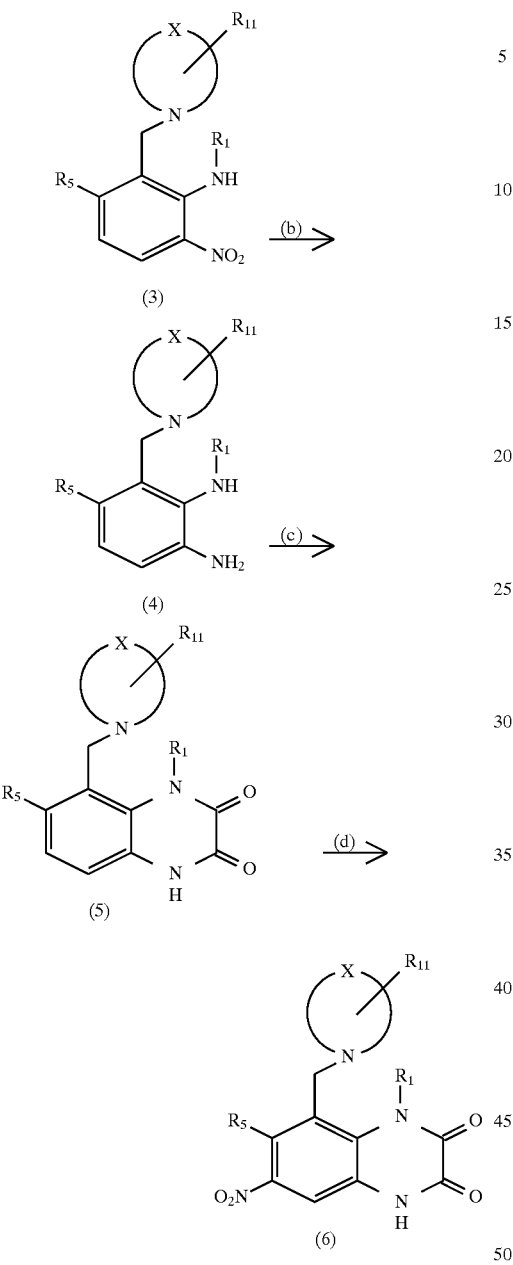

Step (a) of General Scheme I above involves reacting nitroaniline derivative of Formula (1) with amine as depicted in Formula (2) in the presence of triarylphosphine, preferably triphenylphosphine and diester of diazodicarboxylate, preferably diethyldiazodicarboxylate in a solution of a hydrocarbon solvent like benzene or ether solvent like THF, preferably benzene at temperatures around 5° C. The reaction mixture is stirred for 2 to 16 hours and monitored by TLC ($SiO_2$, pet. ether:EtOAc, 1:1). Solvent is evaporated under reduced pressure and product isolated by column chromatography ($SiO_2$, mixture of pet. ether and EtOAc).

Step (b) involves reducing the nitroaniline derivative of Formula (3) via hydrogenolysis ($H_2$, around 50 psi) in the presence of a catalyst like Ra Ni or Pd/C, preferably Ra Ni in a hydroxylated solvent like methanol. The catalyst is filtered off and the filtrate evaporated to give the o-phenylenediamine derivative, which is used in the next step without additional purification.

Step (c) involves reacting the o-phenylenediamine derivative as shown in Formula (4) with oxalic acid derivative like dimethyl oxalate in a hydroxylated solvent like methanol at refluxing temperatures for 12 to 24 hours. The reaction mixture is partially evaporated to give crude product, which is purified by crystallization.

Step (d) involves reacting the quinoxaline-2,3-dione derivative shown in Formula (5) with a nitrating mixture, preferably $KNO_3$ and sulfuric acid or TFA at temperatures ranging from 0° C. to room temperature. The reaction mixture is poured over ice, neutralized with alkali, preferably ammonium hydroxide, and the solid obtained is purified by crystallization or column chromatography ($SiO_2$, pet. ether:EtOAc mixture).

General Scheme II

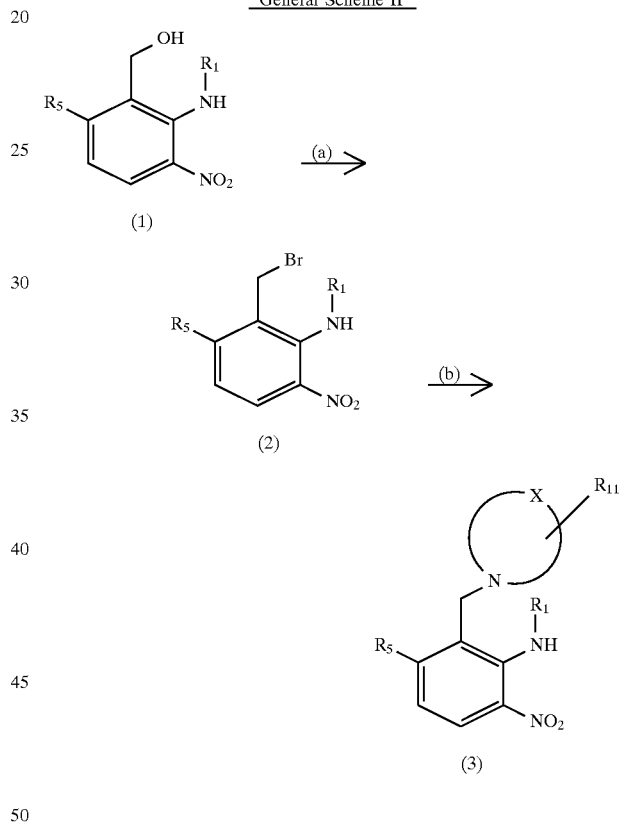

Step (a) in General Scheme II above involves bromination of the nitroaniline derivative shown in formula (1) with brominating agents like $CBr_4/PPh_3$ or $PBr_3$ in a solvent like ether. The volatile materials are evaporated under reduced pressure and the crude product is used directly in step (b) or purified by column chromatography ($SiO_2$, pet. ether:EtOAc mixture).

Step (b) involves reacting the benzyl bromide derivative shown in Formula (2) with appropriate amino compound shown in Structure (3) in the presence of a base like triethylamine in an ether solvent like THF at temperatures ranging from 10°–60° C. The reaction mixture is evaporated to under reduced pressure and quenched with water. Product extracted with a solvent like EtOAc. Final product is purified by column chromatography ($SiO_2$, pet. ether:EtOAc).

Formula (3) in Scheme II can be further derivatized to 4, 5, and 6 in Scheme I.

General Scheme III

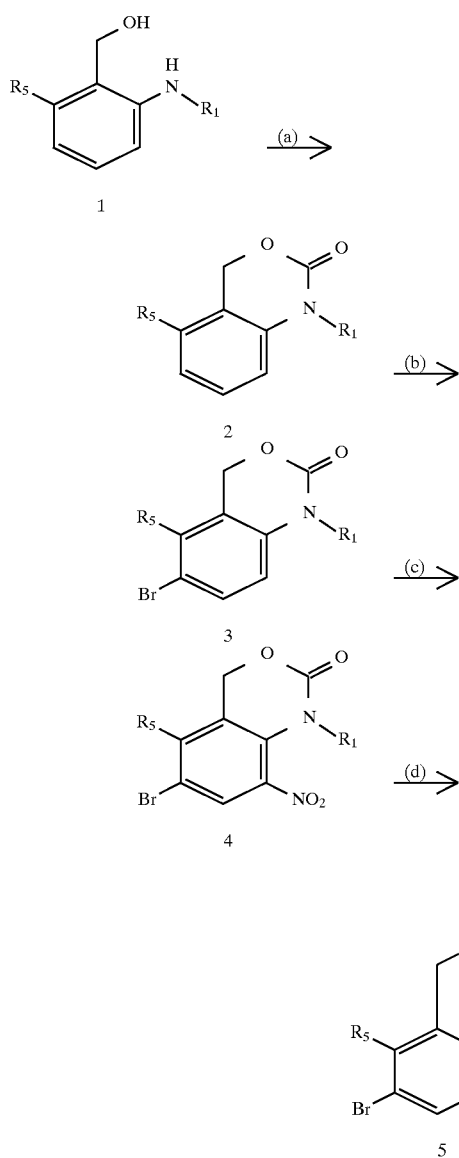

Step (a) in General Scheme III involves reacting an aminoalcohol as shown in formula (1) with phosgene equivalent, preferably phosgene in toluene solution, in the presence of a tertiary base like triethylamine in an ether solvent like tetrahydrofuran. The reaction carried out under stirring at temperatures ranging from 0°–40° C. for 12 to 20 hours, preferably 16 hours. Reaction was subjected to aqueous work-up and product extracted in EtOAc. EtOAc extracts were worked with water and dried over $MgSO_4$. Crude product was purified via crystallization using pet. ether:EtOAc mixture of solvents.

Step (b) involves reacting the cyclic carbamate as shown in formula (2) with a halogenating agent like bromine, preferably bromine in acidic mixture like TFA/AcOH at around 10° C. under stirring. Reaction mixture was poured in ice water after stirring for about 2 hours at room temperature. The product obtained was used further without additional purification.

Step (c) involves nitrating the cyclic carbamate shown in formula (3) with nitrating mixture, preferably $KNO_3$/conc. $H_2SO_4$ at temperatures between −5° to 5° C., preferably 0° C. under stirring. The reaction mixture allowed to warm to room temperature and stirred for 2 to 16 hours, preferably 14 hours, and poured over ice. The precipitate obtained was filtered and used in next step.

Step (d) involves amination of the cyclic carbamate shown in formula (4) using the appropriate amine with or without a solvent. A solvent can be DMF, N-methylformamide, triethyamine, but preferably the amine itself, when amine is a liquid. The reaction mixture was heated to 100°–150° C., preferably the boiling point of the amine, if below 150° C. Volatile materials are removed under vacuo and the final product purified by chromatography ($SiO_2$, using pet. ether:EtOAc mixture in ranging proportions as the solvent).

These general experimental schemes cover most of the final products of the invention. Others are made by known experimental procedures.

The above methodologies can be used to synthesize cyclic amines which are monocycles or bicycles.

SCHEME 1

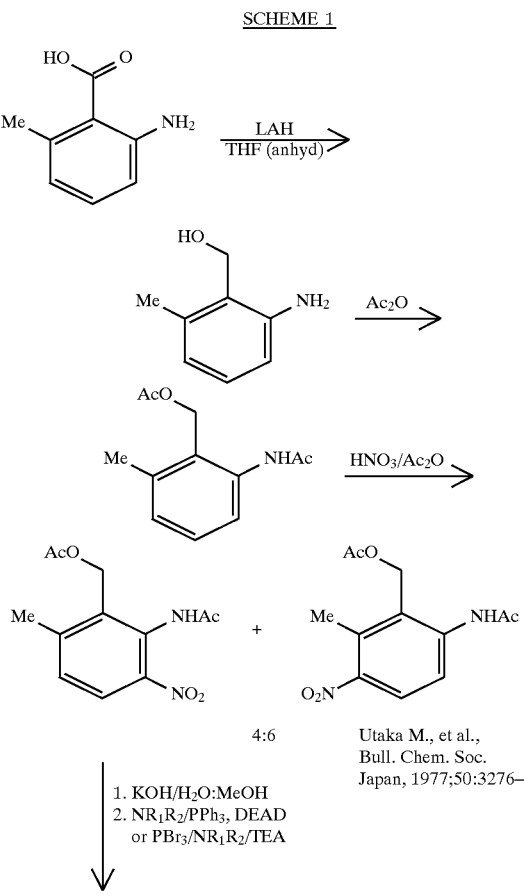

Utaka M., et al.,
Bull. Chem. Soc.
Japan, 1977;50:3276–3280.

SCHEME 1
-continued

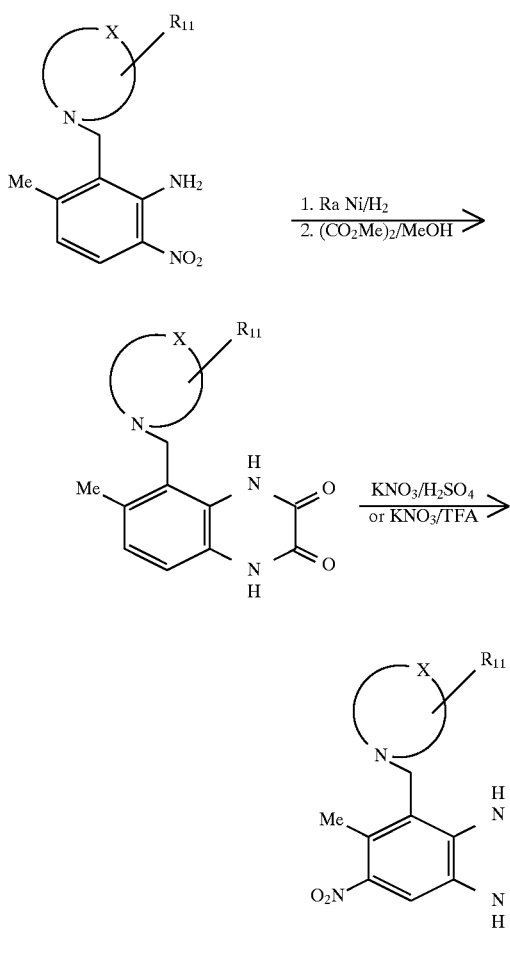

Scheme 1

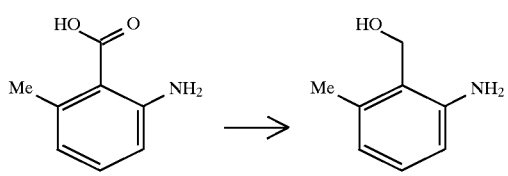

(2-Amino-6-methyl-phenyl)-methanol

2-Amino-6-methyl-benzoic acid (45 g, 300 mmol) was suspended in ether and LAH (13.26 g, 350 mmol), was added portionwise. The reaction mixture was stirred at room temperature for 4 hours and quenched with aqueous NH₄Cl. Reaction mixture was filtered, and the filtrate was extracted with ether (3×200 mL). The wet cake was also washed with ether (200 mL), and the ether solutions were pooled together and washed with water (200 mL) and dried over MgSO₄. Solvent was evaporated to give a crystalline product (19.04 g, 46%), mp 78°–81° C.; MS (CI): M+1=138.

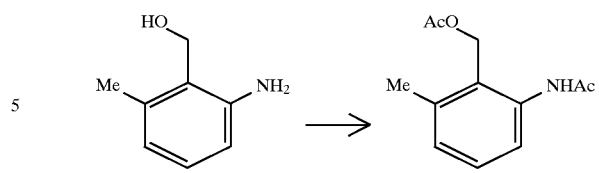

Acetic acid 2-acetylamino-6-methyl-benzyl ester

A solution of (2-amino-6-methyl-phenyl)-methanol (19.04 g, 138.9 mmol) in acetic anhydride (100 mL) was heated to 50° C. for 2 hours. Excess acetic anhydride removed under vacuum to give a pale brown solid, crystallized from CCl₄ (29.8 g, 97%), mp 118°–119° C. (rep. 118°–118.5° C.); MS (CI): M+1=222.

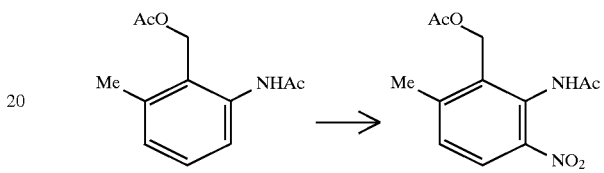

Acetic acid 2-acetylamino-6-methyl-3-nitro-benzyl ester

To a solution of acetic acid 2-acetylamino-6-methyl-benzyl ester in acetic acid (400 mL) nitric acid (60%, 16 mL) was added dropwise keeping temperature below 5° C., under stirring. Reaction mixture was stirred for additional 2 hours at room temperature and poured in ice water and stirred for 0.5 hours. Brown oil separated which on treatment with ethyl acetate (50 mL) gave buff needles, (7.65 g, 18.5%), mp 148°–149° C. (rep. 147°–148° C.); MS (CI): M+1=267.

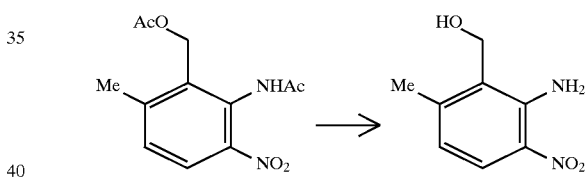

(2-Amino-6-methyl-3-nitro-phenyl)-methanol

Acetic acid 2-acetylamino-6-methyl-3-nitro-benzyl ester (7 g, 26.2 nunol) was dissolved in methanolic KOH (0.5N). The solution was evaporated after 1 hour of stirring at room temperature. Product was extracted in EtOAc (150 mL), washed with water and brine, and dried (MgSO₄). Evaporation of the solvent gave orange needles (4.45 g, 93.4%), mp 134°–136° C. (rep. 135°–136° C.).

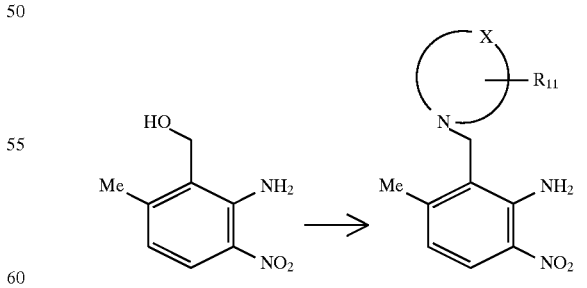

General method for the preparation of cyclic aminomethyl-3-methyl-6-nitro-phenylamine To a suspension of (2-amino-6-methyl-3-nitro-phenyl)-methanol (1 eq.) and PPh₃ (1.5 eq.), and cyclic amine (1.5 eq.) in benzene (10 mL), diethyl azodicarboxylate (DEAD) (1.5 eq.) was added under nitrogen and 5° C. The reaction mixture was allowed to warm to room temperature and stirred for 2 hours. The dark reaction mixture was concentrated under vacuum, and the residue was chromatographed over silica gel (hexanes:ethyl acetate, 95:5 to 75:25) to give the desired product. Various derivatives synthesized are listed in Table 2 above.

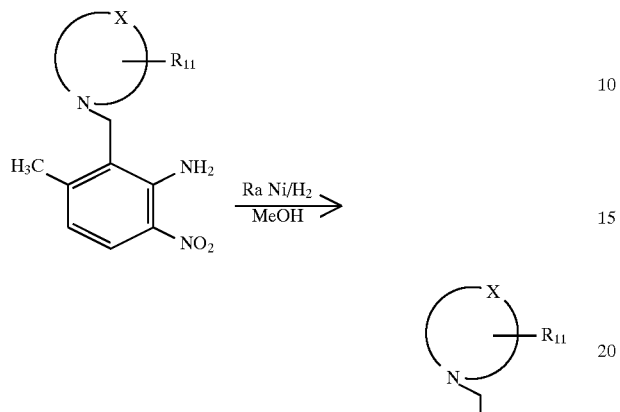

General method for preparation of 3-dialkylamino methyl-4-methyl-benzene-1,2-diamine A solution of 2-(disubstituted aminomethyl-3-methyl-6-nitro-phenylamine (1 eq., approx. 5 mmol) in methanol (75 mL) was hydrogenated ($H_2$, 50 psi) in a Parr apparatus. The reaction was monitored by TLC ($SiO_2$, pet. ether:EtOAc, 1:1) and filtered on completion. The filtrate was concentrated, and the product obtained was used further without additional purification.

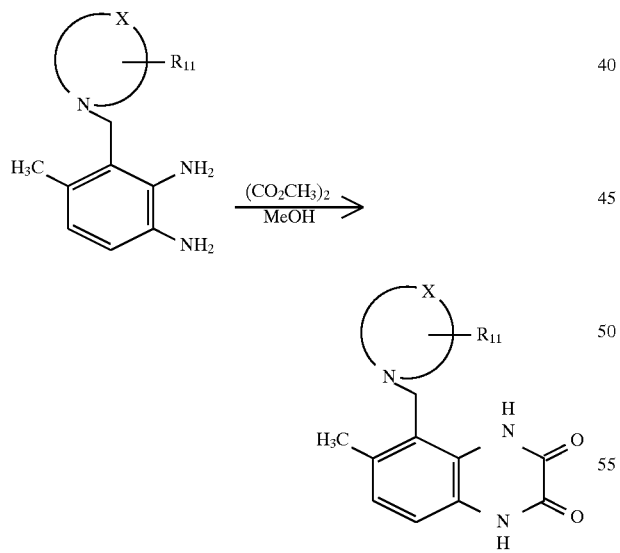

General method for the preparation of 5-dialkylamino methyl-6-methyl-1,4-dihydro-quinoxaline-2,3-dione A solution of 3-dialkylaminomethyl-4-methyl-benzene-1,2-diamine (1 eq.) and dimethyl oxalate (1.5 eq.) in methanol (35 mL) was heated to reflux for 16 hours. The reaction mixture was partially evaporated to give the product as a solid, which was used further without additional purification. The compounds synthesized are listed in Table 3 above.

SCHEME 2

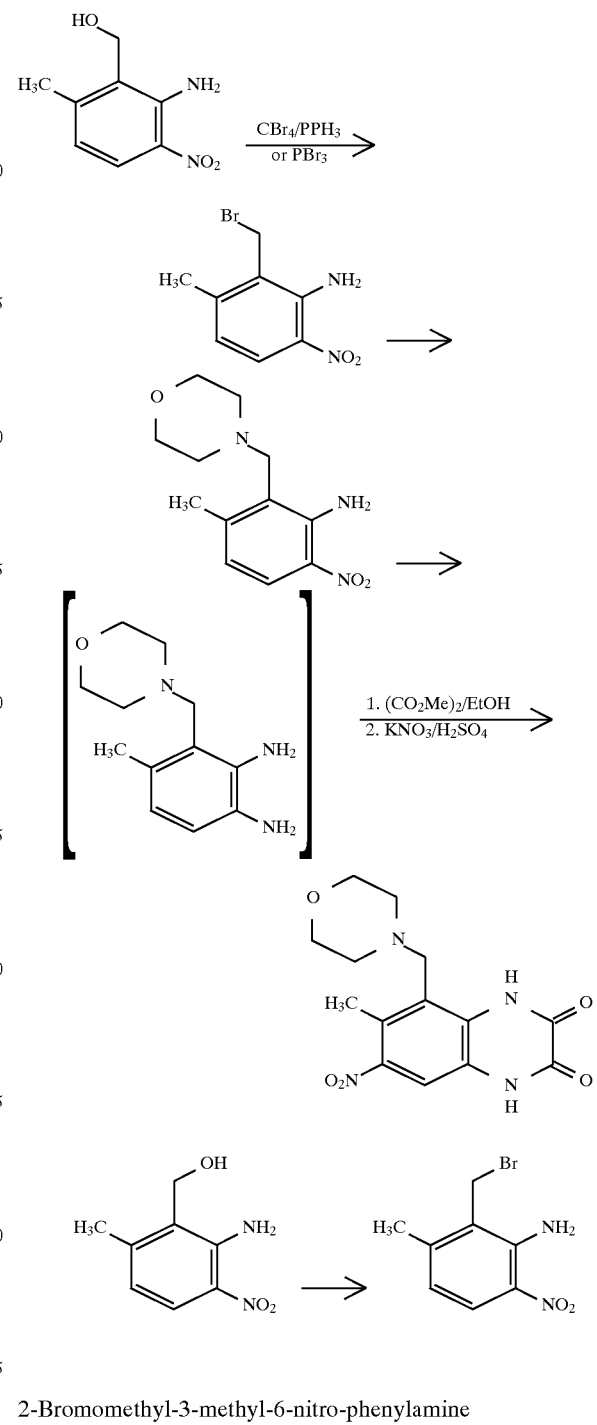

2-Bromomethyl-3-methyl-6-nitro-phenylamine

To a solution of 2-amino-6-methyl-3-nitro-phenyl-methanol (1.09 g, 6 mmol) in ether (10 mL) and THF (25 mL), $PBr_3$ (3.24 g, 12 mmol) was added. Reaction mixture was heated to reflux and after 5 hours evaporated to dryness. Crude product was passed through a short $SiO_2$ column using pet. ether:EtOAc (1:1) as eluent. (Yield: 1.2 g, 82%); HNMR $CDCl_3$: 2.42 (s, 3H), 4.53 (s, 2H), 6.61 (d, 1H, J=8.8 Hz), 8.07 (d, 1H, J=8.8 Hz).

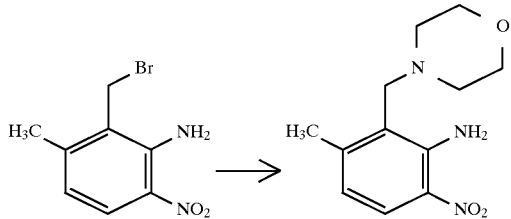

3-Methyl-2-morpholin-4-ylmethyl-6-nitro-phenylamine

To a solution of 2-bromomethyl-3-methyl-6-nitro-phenylamine (1.2 g, 4.9 mmol) in THF (20 mL), morpholine (2 g, 24 mmol) was added. Reaction mixture was stirred for 16 hours at room temperature, and the buff-colored precipitate was filtered, washed, and dried. (Yield: 0.655 g, 43%); MS(CI): M+1=252.

The intermediate 3-methyl-2-morpholin-4-ylmethyl-6-nitro-phenylamine was further converted to the 7-nitro-quinoxaline-2,3-dione analog as indicated in Scheme 1 above.

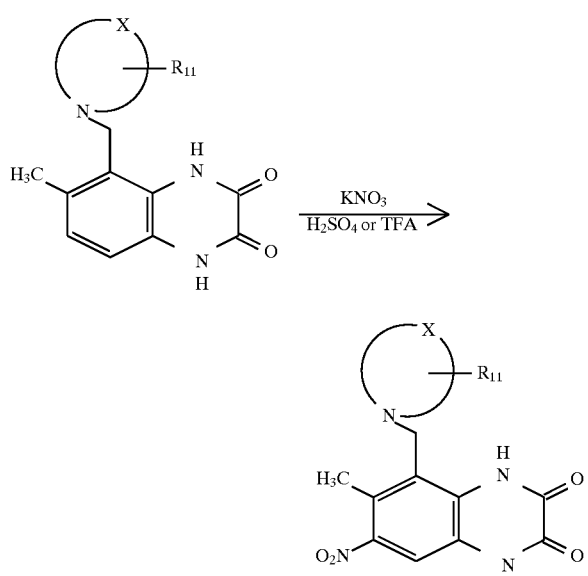

General method for the preparation of 5-dialkylamino methyl-6-methyl-7-nitro-1,4-dihydro-quinoxaline-2,3-dione To a solution of 5-dialkylaminomethyl-6-methyl-1,4-dihydro-quinoxaline-2,3-dione (1 eq., approx. 2–5 mmol) in concentrated $H_2SO_4$ (5 mL) or TFA (5 mL), $KNO_3$ was added at 0° C. under stirring. In case of $H_2SO_4$ as a solvent, reaction mixture was poured over ice, neutralized with alkalai, and the solid obtained crystallized or passed through a column ($SiO_2$, $CHCl_3$, and $CHCl_3$:MeOH 95:5) to give pure product. With TFA as a solvent, excess TFA was evaporated (<35° C.) and solid obtained purified as mentioned above after neutralization with $NH_3$.

The compounds synthesized are listed in Table 4 above.

SCHEME 3

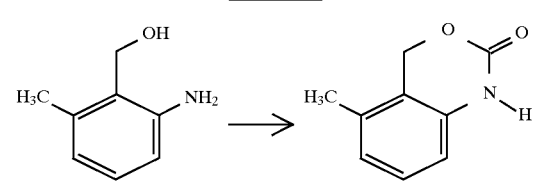

5-Methyl-1,4-dihydro-benzo[d][1,3]-oxazin-2-one

To a solution of (2-amino-6-methyl-phenyl) methanol (2.74 g, 20 mmol) and triethylamine (4.04 g, 40 mmol) in THF (150 mL), phosgene (12.5% solution in toluene, 17.42 g, 22 mmol) was added dropwise at 0° C. Reaction mixture was allowed to warm to room temperature and stirred for 16 hours. Water (150 mL) was added under stirring, followed by EtOAc (2×100 mL). EtOAc extracts were washed with water and brine and dried over $MgSO_4$. The product (buff solid) was crystallized from EtOAc:pet. ether mixture. (Yield: 2.37=73%); (mp 222°–226° C.); MS(CI): M+1=163.

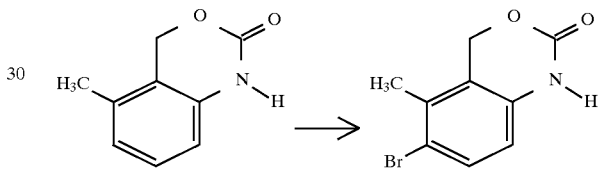

6-Bromo-5-methyl-1,4-dihydro-benzo[d][1,3] oxazine-2-one

To a solution of 5-methyl-1,4-dihydro-benzo[d][1,3] oxazin-2-one (0.695 g, 4.3 mmol) in acetic acid (5 mL), $Br_2$ (0.805 g=5 mmol) solution in TFA (5 mL)+acetic acid (5 mL) was added at 10° C. Reaction mixture was stirred for 2 hours and poured over ice water. Yellow precipitate was filtered and dried at 120° C. (Yield: 0.941 g=90%); MS(CI): M+1=243; M+2=244.

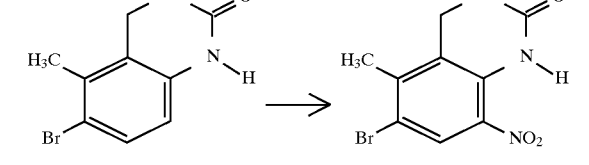

6-Bromo-5-methyl-8-nitro-1,4-dihydro-benzo[d][1,3] oxazin-2-one

To a solution of 6-bromo-5-methyl-1,4-dihydro-benzo [d][1,3] oxazin-2-one (0.726 g, 3 mmol) in conc. $H_2SO_4$ (4 mL), $KNO_3$ (0.303 g, 3 mmol) was added at 0° C. Reaction mixture stirred 14 hours and poured over crushed ice. Yellow precipitate was obtained, which was filtered and dried. (Yield: 0.782=91%); MS(CI):M+1=288; M+2=289.

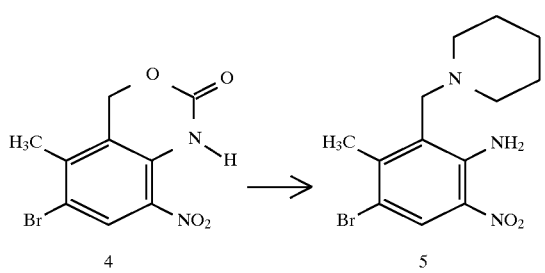

4-Bromo-3-methyl-6-nitro-2-piperidin-1-ylmethyl-phenylamine

A solution of 6-bromo-5-methyl-8-nitro-1,4-dihydro-benzo [d] [1,3] oxazin-2-one (0.184 g, 0.64 mmol) for 8 hours in piperidine (2 mL) was heated to 110° C. The dark reaction mixture was evaporated under vacuum and the crude was chromatographed (SiO$_2$, pet. ether:EtOAc, 9:1→7.5;2.5) to give yellow product. (Yield: 0.154 g, 75%); MS(CI):M+1=326; M+2=327.

The intermediate 5 can be converted to the corresponding quinoxaline-2,3-dione derivative by procedures shown in Scheme 1.

Other compounds prepared by methods analogous to the above include but are not limited to:

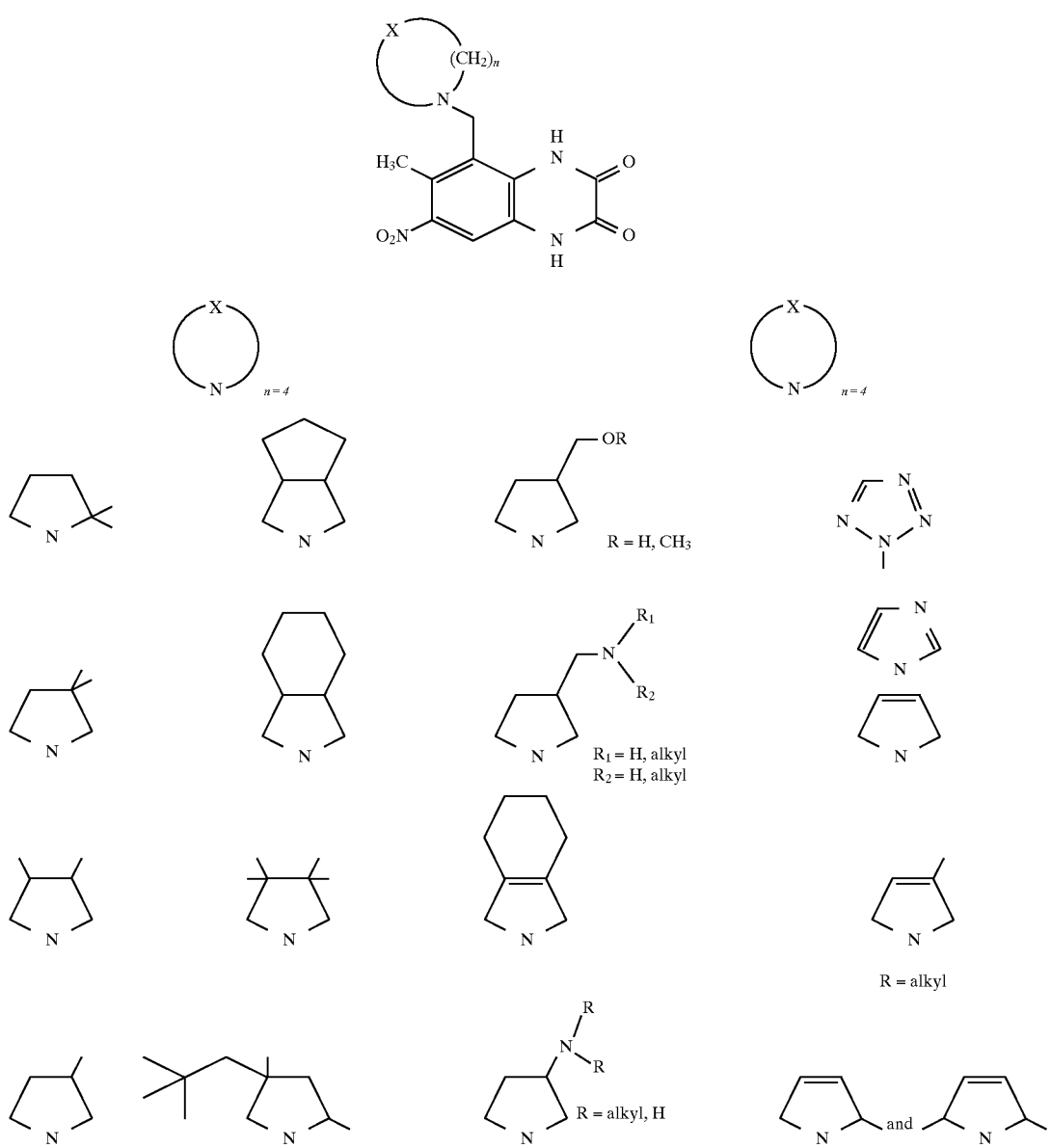

The above cyclic amines are available from commercial sources.
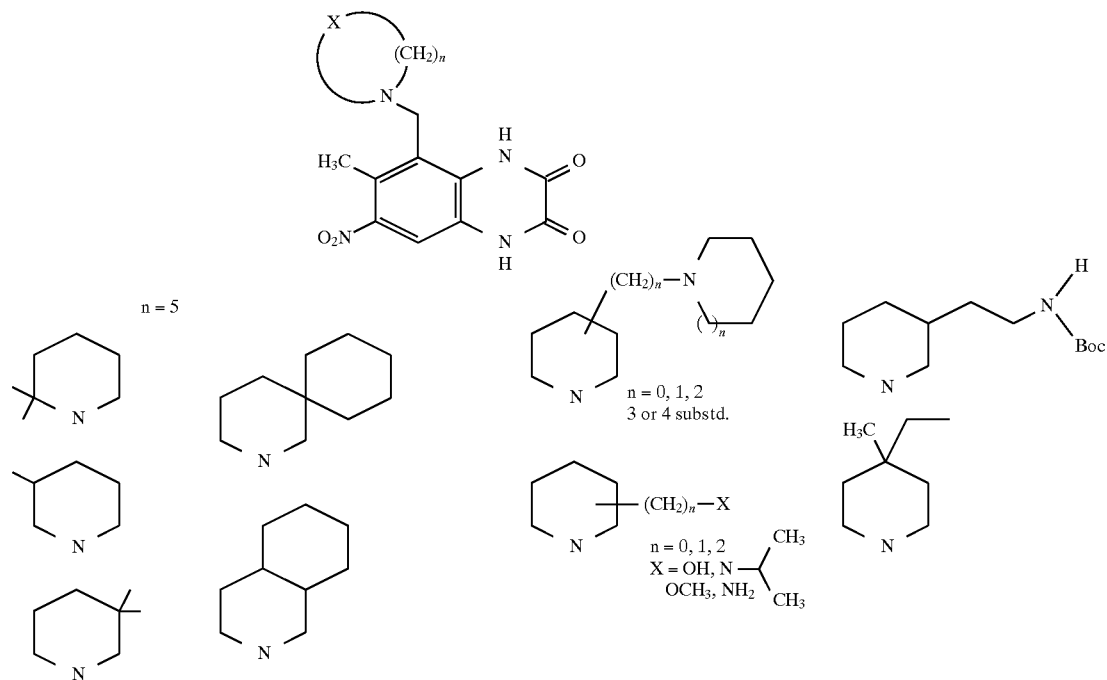
n = 5
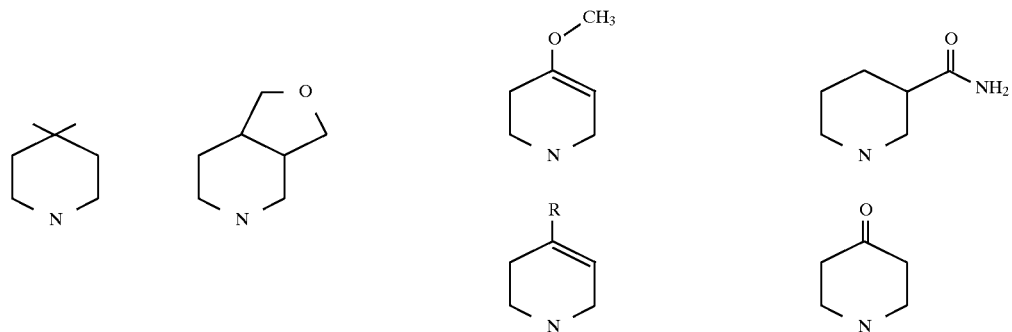
n = 5 (continued)
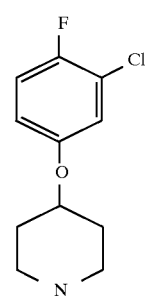
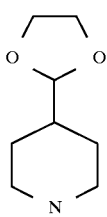
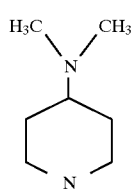
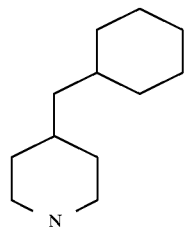

-continued
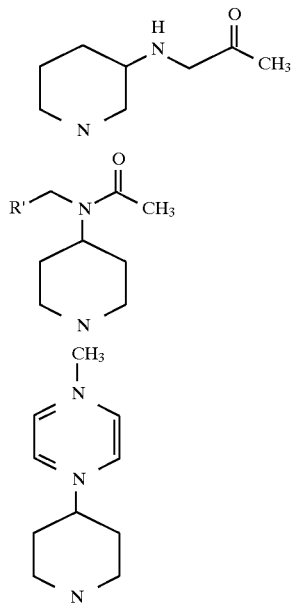
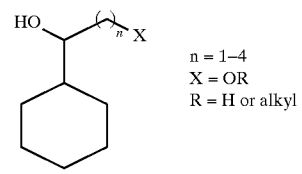
n = 1–4
X = OR
R = H or alkyl
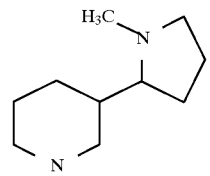
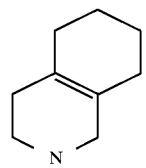
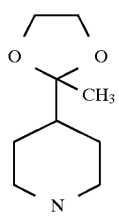
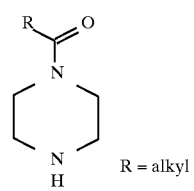
R = alkyl
n = 5 (continued)
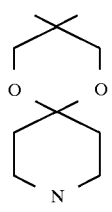
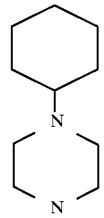
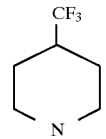
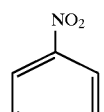
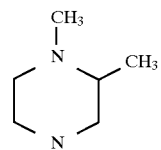
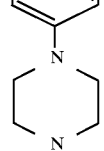
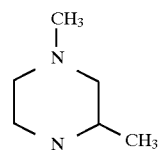
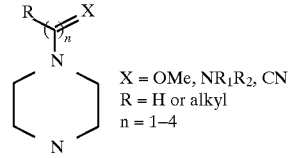
X = OMe, NR$_1$R$_2$, CN
R = H or alkyl
n = 1–4

We claim:
1. A compound of Formula I

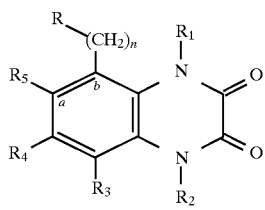

or a pharmaceutically acceptable salt thereof,
wherein
R is a mono-, bi-cycle spiro ring non-aromatic unsubstituted or substituted by from 1 to 4 substituents, R is attached to the quinoxaline ring through (—CH$_2$)$_n$ and at the a- or b-position and
R is

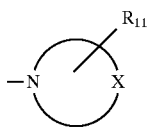

of from 4 to 7 atoms or

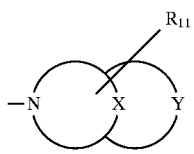

of from 8 to 12 atoms
wherein R$_{11}$ is from 1 to 4 substituents independently selected from
hydrogen,
hydroxy,
hydroxyalky,
alkoxy,
alkoxalkyl,
—NR$_{13}$R$_{14}$,
aminoalkyl,
alkenyl,
alkynyl,
thiol,
alkylthioalkyl,
aryl,
aralkyl,
heteroaryl,
heteroaralkyl,
cycloalkyl,
—SO$_2$R$_{15}$,
—SO$_2$NR$_{13}$R$_{14}$,
—(CH$_2$)$_n$SO$_2$NR$_{13}$R$_{14}$, and
—(CH$_2$)$_n$SO$_2$R$_{15}$,
wherein R$_{13}$ and R$_{14}$ are independently selected from
hydrogen,
alkyl,
cycloalkyl,
heterocycle which is a ring with from 4 to 7 members, with up to 4 heteroatoms selected from N, O, and S,
aralkyl, and
aryl;

R15 is hydroxy, alkoxy, —NR$_{13}$R$_{14}$, or haloalkyl;
R$_{11}$ may be 2 substituents attached at the same carbon;
X and Y are each independently
  carbon which is substituted by hydrogen, halogen, haloalkyl, alkyl, alkoxy, alkoxyalkyl, NR$_{13}$R$_{14}$, aminoalkyl, aralkyl, aryl, heteroaryl, heteroaralkyl, cycloalkyl, heterocycle which is a ring with from 4 to 7 members, with up to 4 heteroatoms selected from N, O, and S, hydroxy, hydroxyalkyl,
  —O—,
  —S—,
  —SO—,
  —SO$_2$—,
  —NR$_{16}$—;
wherein R$_{16}$ is alkyl, hydrogen aralkyl, heteroaralkyl, aryl, herteroaryl, cycloalkyl, heterocycle which is a ring with from 4 to 7 heteroatoms selected from N, O, and S, —C(O)OR$_{17}$, —C(O)R$_{17}$, —SO$_2$NR$_{18}$, —SO$_2$NR$_{19}$R$_{20}$, —CH$_2$SO$_2$R$_{18}$, and —CH$_2$SO$_2$NR$_{19}$R$_{20}$,
wherein R$_{17}$ is alkyl, aralkyl, cycloalkyl, heterocycle which is a ring with from 4 to 7 heteroatoms selected from N, O, and S, aryl, or heteroaryl;
R$_{18}$ is alkyl, aralkyl, hydroxyl, or alkoxy;
R$_{19}$ and R$_{20}$ are each independently hydrogen and alkyl;
n is an integer of from, 1 to 4;
R$_1$ is hydrogen,
  alkyl,
  aralkyl,
  carboxyalkyl, or
  phosphonoalkyl,
R$_2$ is hydrogen, hydroxy, or amino,
R$_3$ and R$_4$ are each independently
  hydrogen,
  alkyl,
  cycloalkyl,
  alkenyl,
  halogen,
  haloalkyl,
  nitro,
  cyano,
  SO$_2$CF$_3$,
  CH$_2$SO$_2$R$_6$,
  (CH$_2$)$_m$CO$_2$R$_6$,
  (CH$_2$)$_m$CONR$_7$R$_8$,
  (CH$_2$)$_m$SO$_2$NR$_7$R$_8$, or
  NHCOR$_6$ wherein m is an integer of from 0 to 4, and R$_6$, R$_7$, and R$_8$ are each independently selected from hydrogen, alkyl cycloalkyl, haloalkyl, or aralkyl;
R$_5$ is hydrogen,
  alkyl,
  alkenyl,
  cycloalkyl,
  halogen,
  haloalkyl,
  aryl,
  aralkyl,
  heteroaryl,
  nitro,
  cyano,
  SO$_2$CF$_3$,
  (CH$_2$)$_m$CO$_2$R$_9$,
  (CH$_2$)$_m$CONR$_9$R$_{10}$,
  SONR$_9$R$_{10}$, or
  NHCOR$_9$;

wherein m is an integer of from 0 to 4;
R₉ and R₁₀ are each independently hydrogen, alkyl, cycloalkyl, haloalkyl, or aralkyl; and
R₅ may be at the a-position and R—(CH₂)— at the b-position on the ring.

2. A compound according to claim 1 wherein R is

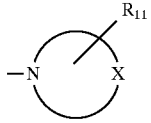

of from 4 to 7 atoms where
x is
carbon substituted by hydrogen, haloalkyl, alkyl, alkoxy, alkoxyalkyl, NR₁₃R₁₄, aminoalkyl, cycloalkyl, heterocycloalkyl, hydroxy, and hydroxyalkyl,
—O—,
—NR₁₆—, and
—C(O)—;
R₁₁ is absent,
hydrogen,
alkyl,
alkoxy,
alkoxyalkyl, NR₁₃R₁₄,
aminoalkyl,
aralkyl,
aryl,
heteroaryl,
heteroaralkyl,
cycloalkyl,
heterocycloalkyl,
hydroxy, or
hydroxyalkyl;
R₁₁ may also represent two independent alkyl substituents to form a gem-dialkyl arrangement, and
where X represents carbon, an integral double bond may be located between the C₃ and C₄ carbons of 5- to 7-membered rings.

3. A compound according to claim 1 wherein R is

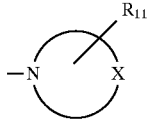

of from 4 to 7 atoms wherein
X is
carbon substituted by hydrogen, alkyl, NR₁₃R₁₄, aminoalkyl, cycloalkyl, and heterocycloalkyl,
—O—,
—NR₁₆—,
—C(O)—, and
R¹¹ is absent,
hydrogen,
alkyl,
alkoxy,
alkoxyalkyl,
NR₁₃R₁₄,
aminoalkyl,
cycloalkyl,
heterocycloalkyl,
hydroxy, or
hydroxyalkyl;
R₁₁ may also represent 2 independent alkyl substituents to form a gem-dialkyl arrangement, and
where X represents carbon, an integral double bond may be located between the C₃ and C₄ carbons of 5- to 7-membered rings.
R₁ is hydrogen;
R₂ is hydrogen or hydroxy;
R₃ and R₄ are each independently
hydrogen,
alkyl, and
nitro;
R₅ is hydrogen,
alkyl,
cycloalkyl,
halogen, and
nitro.

4. A compound according to claim 3 selected from:
6-Methyl-5-pyrrolidin-1-ylmethyl-7-nitro-1,4-dihydroquinoxaline-2,3-dione,
6-Methyl-5-(2-methyl-pyrrolidin-1-ylmethyl)-7-nitro-1,4-dihydroquinoxaline-2,3-dione,
5-(2,5-Dimethyl-pyrrolidin-1-ylmethyl)-6-methyl-7-nitro-1,4-dihydroquinoxaline-2,3-dione,
6-Methyl-5-(2-methyl-piperidin-1-ylmethyl)-7-nitro-1,4-dihydroquinoxaline-2,3-dione,
6-Methyl-5-(4-methyl-piperidin-1-ylmethyl)-7-nitro-1,4-dihydroquinoxaline-2,3-dione,
5-(3,5-Dimethyl-piperidin-1-ylmethyl)-6-methyl-7-nitro-1,4-dihydroquinoxaline-2,3-dione,
5-(3-Azaspiro [5.5] undec-3-ylmethyl)-6-methyl-7-nitro-1,4-dihydroquinoxaline-2,3-dione,
5-(1,4-Dioxa-8-azaspiro [4,5] dec-8-ylmethyl)-6-methyl-7-nitro-1,4-dihydroquinoxaline-2,3-dione,
6-Methyl-5-morpholin-4-ylmethyl-7-nitro-1,4-dihydroquinoxaline-2,3-dione,
6-Methyl-5-(4-methyl-piperazin-1-ylmethyl)-7-nitro-1,4-dihydroquinoxaline-2,3-dione,
5-Azepan-1-ylmethyl-6-methyl-7-nitro-1,4-dihydroqinoxaline-2,3-dione,
6-Methyl-7-nitro-5-(octahydroquinolin-1-ylmethyl)-1,4-dihydroquinoxaline-2,3-dione, and
6-Methyl-7-nitro-5-(octahydroisoquinolin-2-ylmethyl)-1,4-dihydroquinoxaline-2,3-dione.

5. A compound named
6-Methyl-7-nitro-5-pyrrolidine-1-ylmethyl-1,4-dihydroquinoxaline-2,3-dione, and
6-Methyl-7-nitro-5-piperidin-1-ylmethyl-1,4-dihydroquinoxaline-2,3-dione.

6. A compound according to claim 1 wherein R is

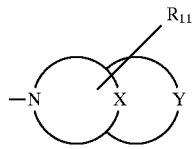

of from 8 to 12 atoms wherein
X and Y are each independently
carbon which is substituted by hydrogen, halogen, haloalkyl, alkyl, alkoxy, alkoxyalkyl, NR₁₃R₁₄, aminoalkyl, aralkyl, aryl, heteroaryl, heteroaralkyl, cycloalkyl, heterocycloalkyl, hydroxy, hydroxyalkyl, —O—,
—SO$_2$—,
—NR$_{16}$—;
  wherein R$_{16}$ is alkyl, hydrogen, aralkyl, heteroaralkyl, aryl, heteroaryl, cycloalkyl, heterocycloalkyl, —C(O)OR$_{17}$, —C(O)R$_{17}$, —SO$_2$R$_{18}$, —SO$_2$NR$_{19}$R$_{20}$, —CH$_2$SO$_2$R$_{18}$, and —CH$_2$SO$_2$NR$_{19}$R$_{20}$,
    wherein R$_{17}$ is alkyl, aralkyl, cycloalkyl, heterocycloalkyl, aryl, or heteroaryl;
  R$_{18}$ is alkyl, aralkyl, hydroxyl, or alkoxy;
  R$_{19}$ and R$_{20}$ are each independently hydrogen and alkyl;

R$_{11}$ is absent,
  hydrogen,
  alkyl,
  alkoxy,
  alkoxyalkyl,
  NR$_{13}$R$_{14}$,
  aminoalkyl,
  aralkyl,
  aryl,
  heteroaryl,
  heteroarakyl,
  cycloalkyl,
  heterocycloalkyl,
  hydroxy, and
  hydroxyalkyl;

R$_1$ is hydrogen;

R$_2$ is hydrogen or hydroxy;

R$_3$ and R$_4$ are each independently
  hydrogen,
  alkyl,
  nitro; and

R$_5$ is hydrogen,
  alkyl,
  cycloalkyl,
  halogen, and
  nitro.

7. A pharmaceutical composition comprising a compound according to claim 1 together with a pharma- ceutically acceptable carrier in unit dosage form.

8. A method for treating stroke which comprises administering a therapeutically effective amount of a compound according to claim 1 to a patient in need of said treatment.

9. A method for treating cerebral hypoxia/ischemia which comprises administering a therapeutically effective amount of a compound according to claim 1 to a patient in need of said treatment.

* * * * *

UNITED STATES PATENT AND TRADEMARK OFFICE
CERTIFICATE OF CORRECTION

PATENT NO. : 5,874,426
DATED : Feb. 23 1999
INVENTOR(S) : Kornberg et al.

It is certified that error appears in the above-identified patent and that said Letters Patent is hereby corrected as shown below:

Column 51, line 14, "bi-cyclc" should read "bi-cyclic".

Column 51, line 40, "hydroxyalky," should read "hydroxyalkyl".

Column 51, line 40, after "hydroxyalkyl," insert "alkyl,".

Column 51, line 43, "alkoxalkyl," should read "alkoxyalkyl".

Column 52, line 1, "R15" should read "$R_{15}$".

Column 52, line 15, insert a "," after "hydrogen".

Column 52, line 16, "herteroaryl" should read "heteroaryl".

Column 52, line 18, "-$SO_2NR_{18}$," should read "-$SO_2R_{18}$,".

Column 52, line 27, delete the "," after "from".

Signed and Sealed this

Twenty-seventh Day of February, 2001

Attest:

NICHOLAS P. GODICI

Attesting Officer     Acting Director of the United States Patent and Trademark Office